(12) United States Patent
Chan et al.

(10) Patent No.: US 8,643,274 B2
(45) Date of Patent: Feb. 4, 2014

(54) METHODS FOR CHEMICAL EQUIVALENCE IN CHARACTERIZING OF COMPLEX MOLECULES

(75) Inventors: Hardy Chan, San Mateo, CA (US); Jentaie Shiea, Kaohsiung (TW)

(73) Assignee: Scinopharm Taiwan, Ltd., Tainan (TW)

( * ) Notice: Subject to any disclaimer, the term of this patent is extended or adjusted under 35 U.S.C. 154(b) by 359 days.

(21) Appl. No.: 13/014,198

(22) Filed: Jan. 26, 2011

(65) Prior Publication Data

US 2011/0183426 A1  Jul. 28, 2011

Related U.S. Application Data

(63) Continuation-in-part of application No. 12/775,747, filed on May 7, 2010.

(60) Provisional application No. 61/298,367, filed on Jan. 26, 2010.

(51) Int. Cl.
*H01J 17/26* (2012.01)

(52) U.S. Cl.
USPC .............................. 313/564; 435/4

(58) Field of Classification Search
USPC .............................. 313/564; 435/4
See application file for complete search history.

(56) References Cited

U.S. PATENT DOCUMENTS

2006/0172429 A1   8/2006 Nilsson et al.

FOREIGN PATENT DOCUMENTS

WO   WO 2007/127977   11/2007

OTHER PUBLICATIONS

Bongers et al. "Validation of a peptide mapping method for a therapeutic monoclonal antibody: what could we possible learn about a method we have run 100 times?", J of Pharmaceutical and Biomedical Analysis, 2000, 21:1099-1128.*
Kurogochi et al. "Structural Characterization of N-glycopeptides by matrix-dependent selective fragmentation of MALDI-TOF/ TOF tandem mass spectrometry", Anal. Chem. 2004, 76:6097-6101.*
Marego et al. "Study of proteomic changes associated with healthy and tumoral murine samples in neuroblastoma by principal component analysis and classification methods", Clinica Chimica Acta, 2004, 345:55-67.*
Zamani et al. "Conformational studies of a monoclaonal antibody, IgG1, by chemical oxidation: structural analysis by ultrahigh-pressure LC-electrospray ionization time-of-flight MS and multivariate data analysis", Analytical Biochemistry, 2008, 380(2):155-163.*
Bryant et al. "Principal component analysis of mass spectra of peptides generated from the tryptic digestion of protein mixtures", Rapid Communications in Mass Spectrometry, 2001, 15:418-427.*
Ou et al., Solvent and acidity effects on the UV-visible spectra and protonation-deprotonation of free-base octaethylcorrole. Journal of Prophyrins and Pthalocyanines (2008) vol. 12, No. 1 p. 1-10.
International Search Report dated Jul. 19, 2010.

* cited by examiner

*Primary Examiner* — Bin Shen
(74) *Attorney, Agent, or Firm* — Enshan Hong; Kent H. Cheng; VLP Law Group LLP

(57) ABSTRACT

The present invention provides for a method of characterizing and classifying a sample containing a complex molecule, such as a peptide or polypeptide mixture, protein, protein mixture, biologic and biosimilar by using physical analysis, such as mass spectrometry, and statistic methods.

4 Claims, 55 Drawing Sheets

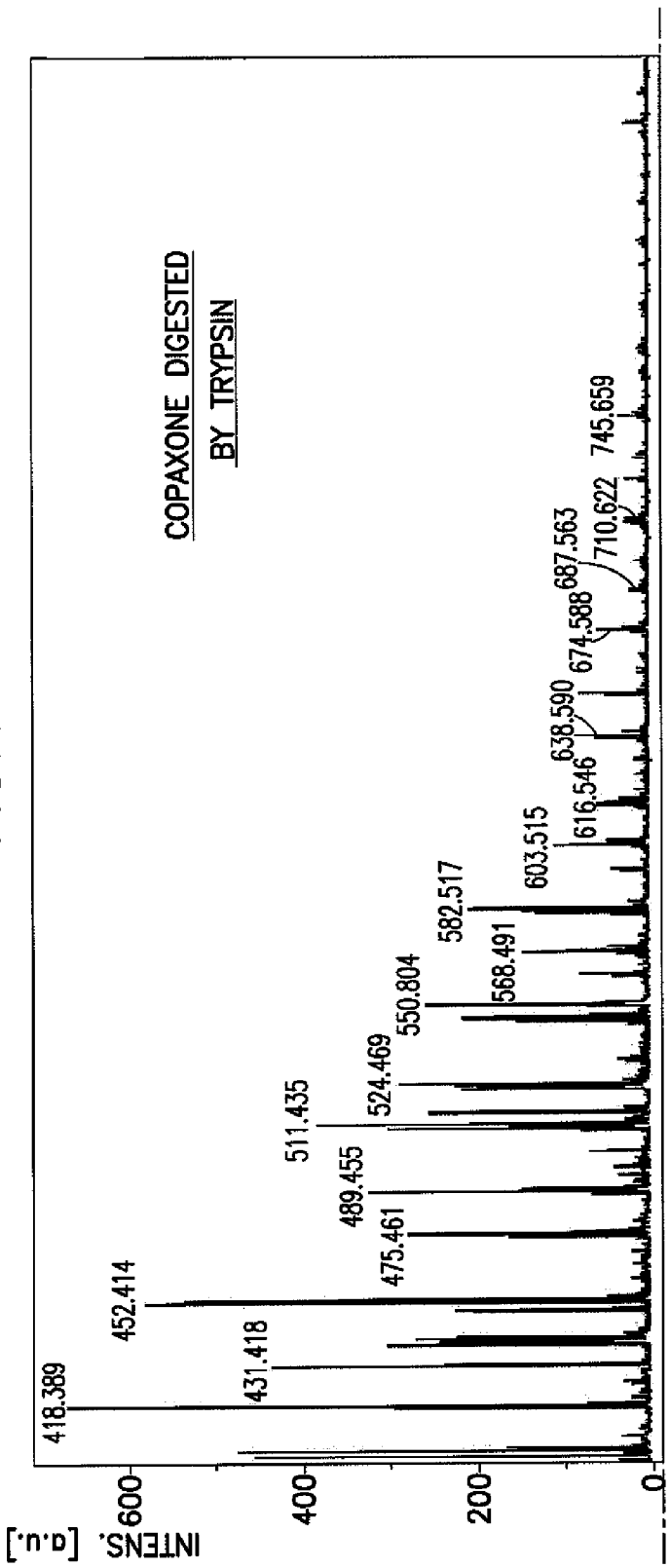

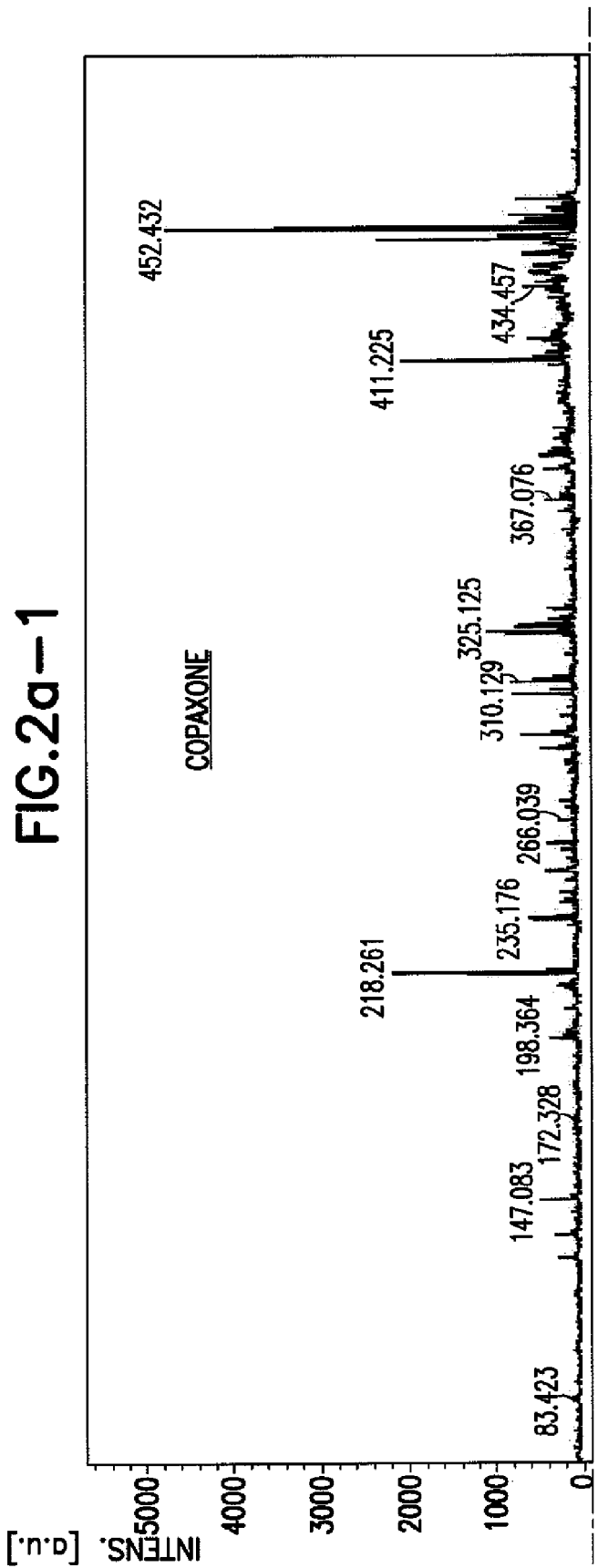

| Ion | | | | | Tyr | Ala | Ala | Lys |
|---|---|---|---|---|---|---|---|---|
| | Y | A | A | K | 1 | 2 | 3 | 4 |
| a | Y | A | A | K | 136.076 | 207.113 | 278.150 | 406.245 |
| b | Y | A | A | K | 164.071 | 235.108 | 306.145 | 434.240 |
| a-17 | Y | A | A | K | 119.049 | 190.086 | 261.123 | 389.218 |
| a-18 | Y | A | A | K | 118.065 | 189.102 | 260.139 | 388.234 |
| b-17 | Y | A | A | K | 147.044 | 218.081 | 289.118 | 417.213 |
| b-18 | Y | A | A | K | 146.060 | 217.097 | 288.134 | 416.229 |
| b+18 | Y | A | A | K | 182.081 | 253.118 | 324.155 | 452.250 |
| y | Y | A | A | K | 147.113 | 218.150 | 289.187 | 452.250 |
| y-17 | Y | A | A | K | 130.110 | 201.147 | 272.184 | 435.248 |
| i | Y | A | A | K | 136.076 | 44.049 | 44.049 | 101.107 |
| | 4 | 3 | 2 | 1 | Lys | Ala | Ala | Tyr |

FIG.2b-1

| FIG.2b-1A |
|---|
| FIG.2b-1B |

FIG.2b-1B

| Ion | Y | A | A | K | Tyr | Ala | Ala | Lys |
|---|---|---|---|---|---|---|---|---|
| | 1 | 2 | 3 | 4 | 1 | 2 | 3 | 4 |
| a | Y | A | A | K | 136.076 | 207.113 | 278.150 | 406.245 |
| a-17 | Y | A | A | K | 119.049 | 190.086 | 261.123 | 389.218 |
| a-18 | Y | A | A | K | 118.065 | 189.102 | 260.139 | 388.234 |
| b | Y | A | A | K | 164.071 | 235.108 | 306.145 | 434.240 |
| b-17 | Y | A | A | K | 147.044 | 218.081 | 289.118 | 417.213 |
| b-18 | Y | A | A | K | 146.060 | 217.097 | 288.134 | 416.229 |
| b+18 | Y | A | A | K | 182.081 | 253.118 | 324.155 | 452.250 |
| c | Y | A | A | K | 181.097 | 252.134 | 323.171 | 451.266 |
| x | Y | A | A | K | 173.092 | 244.129 | 315.166 | 478.230 |
| y | Y | A | A | K | 147.113 | 218.150 | 289.187 | 452.250 |
| z | Y | A | A | K | 130.086 | 201.123 | 272.160 | 435.224 |
| i | Y | A | A | K | 136.076 | 44.049 | 44.049 | 101.107 |
| | 4 | 3 | 2 | 1 | Lys | Ala | Ala | Tyr |

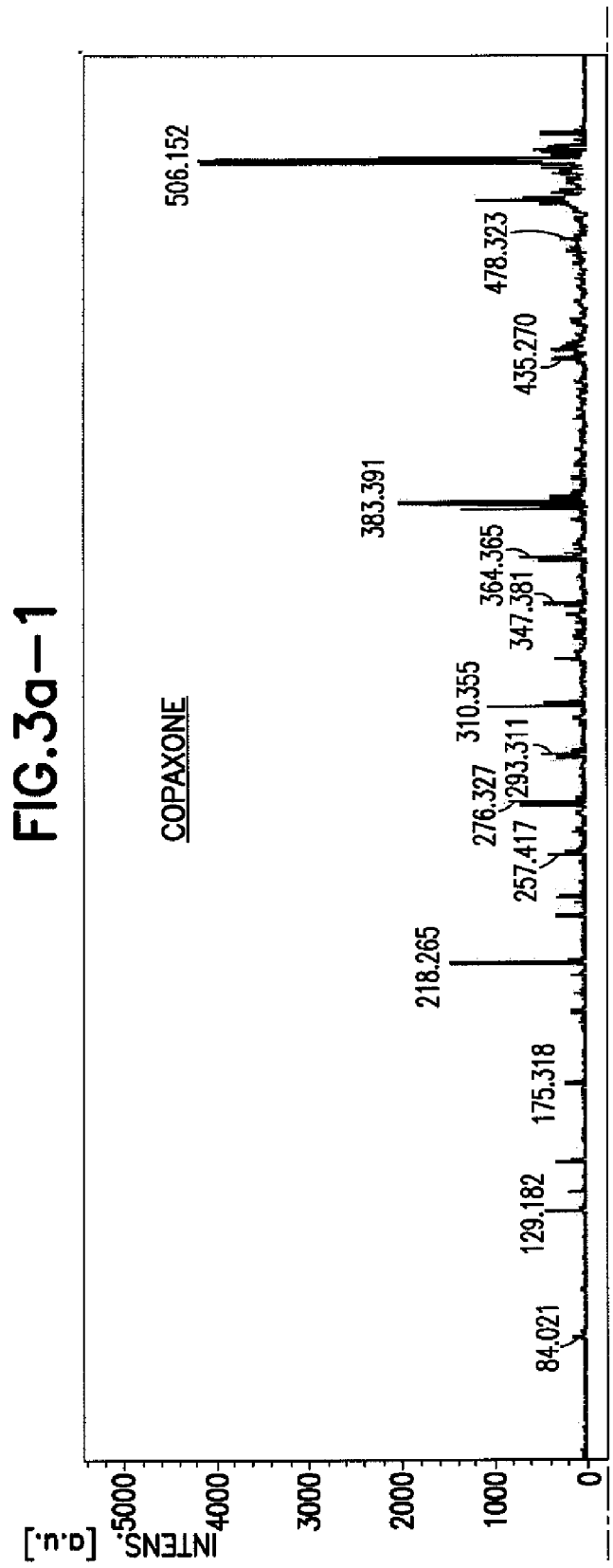

| Ion | E | A | Y | K | Glu | Ala | Tyr | Lys |
|---|---|---|---|---|---|---|---|---|
|  | 1 | 2 | 3 | 4 |  | 2 | 3 | 4 |
|  |  |  |  |  | 1 |  |  |  |
| a | E | A | Y | K | 102.055 | 173.092 | 336.155 | 464.250 |
| a-17 | E | A | Y | K | 85.028 | 156.066 | 319.129 | 447.224 |
| a-18 | E | A | Y | K | 84.044 | 155.082 | 318.145 | 446.240 |
| b | E | A | Y | K | 130.050 | 201.087 | 364.150 | 492.245 |
| b-17 | E | A | Y | K | 113.023 | 184.060 | 347.124 | 475.219 |
| b-18 | E | A | Y | K | 112.039 | 183.076 | 346.140 | 474.235 |
| b+18 | E | A | Y | K | 148.060 | 219.098 | 382.161 | 510.256 |
| c | E | A | Y | K | 147.076 | 218.114 | 381.177 | 509.272 |
| x | E | A | Y | K | 173.092 | 336.155 | 407.193 | 536.235 |
| y | E | A | Y | K | 147.113 | 310.176 | 381.213 | 510.256 |
| z | E | A | Y | K | 130.086 | 293.150 | 364.187 | 493.229 |
| i | E | A | Y | K | 102.055 | 44.049 | 136.075 | 101.107 |
|  | 4 | 3 | 2 | 1 | Lys | Tyr | Ala | Glu |

FIG.3b—1B

| FIG.3b—1A |
|---|
| FIG.3b—1B |

FIG.3b—1

| Ion | E | A | Y | K | Glu | Ala | Ala | Lys |
|---|---|---|---|---|---|---|---|---|
| | | | | | 1 | 2 | 3 | 4 |
| a | E | A | Y | K | 102.055 | 173.092 | 336.155 | 464.250 |
| b | E | A | Y | K | 130.050 | 201.087 | 364.150 | 492.245 |
| a-17 | E | A | Y | K | 85.028 | 156.066 | 319.129 | 447.224 |
| a-18 | E | A | Y | K | 84.044 | 155.082 | 318.145 | 446.240 |
| b-17 | E | A | Y | K | 113.023 | 184.060 | 347.124 | 475.219 |
| b-18 | E | A | Y | K | 112.039 | 183.076 | 346.140 | 474.235 |
| b+18 | E | A | Y | K | 148.060 | 219.098 | 382.161 | 510.256 |
| y | E | A | Y | K | 147.113 | 310.176 | 381.213 | 510.256 |
| y-17 | E | A | Y | K | 130.110 | 293.173 | 364.211 | 493.253 |
| i | E | A | Y | K | 102.055 | 44.049 | 136.075 | 101.107 |
| | 4 | 3 | 2 | 1 | Lys | Tyr | Ala | Glu |

| Ion | Y | E | A | K | | Tyr | Glu | Ala | Lys |
|---|---|---|---|---|---|---|---|---|---|
| | 1 | 2 | 3 | 4 | | 1 | 2 | 3 | 4 |
| a | Y | E | A | K | | 136.076 | 265.118 | 336.155 | 464.250 |
| a-17 | Y | E | A | K | | 119.049 | 248.092 | 319.129 | 447.224 |
| a-18 | Y | E | A | K | | 118.065 | 247.108 | 318.145 | 446.240 |
| b | Y | E | A | K | | 164.071 | 293.113 | 364.150 | 492.245 |
| b-17 | Y | E | A | K | | 147.044 | 276.087 | 347.124 | 475.219 |
| b-18 | Y | E | A | K | | 146.060 | 275.103 | 346.140 | 474.235 |
| b+18 | Y | E | A | K | | 182.081 | 311.124 | 382.161 | 510.256 |
| c | Y | E | A | K | | 181.097 | 310.140 | 381.177 | 509.272 |
| x | Y | E | A | K | | 173.092 | 244.129 | 373.172 | 536.235 |
| y | Y | E | A | K | | 147.113 | 218.150 | 347.193 | 510.256 |
| z | Y | E | A | K | | 130.086 | 201.123 | 330.166 | 493.229 |
| i | Y | E | A | K | | 136.076 | 102.054 | 44.049 | 101.107 |
| | 4 | 3 | 2 | 1 | | Lys | Ala | Glu | Tyr |

| Ion | Y | E | A | K | Tyr | Glu | Ala | Lys |
|---|---|---|---|---|---|---|---|---|
| | 1 | 2 | 3 | 4 | 1 | 2 | 3 | 4 |
| a | Y | E | A | K | 136.076 | 265.118 | 336.155 | 464.250 |
| b | Y | E | A | K | 164.071 | 293.113 | 364.150 | 492.245 |
| a-17 | Y | E | A | K | 119.049 | 248.092 | 319.129 | 447.224 |
| a-18 | Y | E | A | K | 118.065 | 247.108 | 318.145 | 446.240 |
| b-17 | Y | E | A | K | 147.044 | 276.087 | 347.124 | 475.219 |
| b-18 | Y | E | A | K | 146.060 | 275.103 | 346.140 | 474.235 |
| b+18 | Y | E | A | K | 182.081 | 311.124 | 382.161 | 510.256 |
| y | Y | E | A | K | 147.113 | 218.150 | 347.193 | 510.256 |
| y-17 | Y | E | A | K | 130.110 | 201.147 | 330.190 | 493.253 |
| i | | | | | 136.076 | 102.054 | 44.049 | 101.107 |
| | 4 | 3 | 2 | 1 | Lys | Ala | Tyr | Tyr |

|     | K | A | E | K | K |     | Lys | Ala | Glu | Lys | Lys |
|-----|---|---|---|---|---|-----|-----|-----|-----|-----|-----|
| Ion | 1 | 2 | 3 | 4 | 5 |     | 1   | 2   | 3   | 4   | 5   |
| a   | K | A | E | K | K |     | 101.107 | 172.144 | 301.187 | 429.282 | 557.377 |
| a-17 | K | A | E | K | K |    | 84.081 | 155.118 | 284.160 | 412.255 | 540.350 |
| a-18 | K | A | E | K | K |    | 83.097 | 154.134 | 283.176 | 411.271 | 539.366 |
| b   | K | A | E | K | K |     | 129.102 | 200.139 | 329.182 | 457.277 | 585.372 |
| b-17 | K | A | E | K | K |    | 112.076 | 183.113 | 312.155 | 440.250 | 568.345 |
| b-18 | K | A | E | K | K |    | 111.092 | 182.129 | 311.171 | 439.266 | 567.361 |
| b+18 | K | A | E | K | K |    | 147.113 | 218.150 | 347.193 | 475.287 | 603.382 |
| c   | K | A | E | K | K |     | 146.129 | 217.166 | 346.208 | 474.303 | 602.398 |
| x   | K | A | E | K | K |     | 173.092 | 301.187 | 430.230 | 501.267 | 629.362 |
| y   | K | A | E | K | K |     | 147.113 | 275.208 | 404.250 | 475.287 | 603.382 |
| z   | K | A | E | K | K |     | 130.086 | 258.181 | 387.224 | 458.261 | 586.356 |
| i   | K | A | E | K | K |     | 101.107 | 44.049 | 102.054 | 101.107 | 101.107 |
|     | 5 | 4 | 3 | 2 | 1 |     | Lys | Lys | Glu | Ala | Lys |

|     | K | A | E | K | K |
| --- | - | - | - | - | - |
|     | 1 | 2 | 3 | 4 | 5 |
| Ion | Lys | Ala | Glu | Lys | Lys |
|     | 1 | 2 | 3 | 4 | 5 |
| a     | 101.107 | 172.144 | 301.187 | 429.282 | 557.377 |
| a-17  | 84.081  | 155.118 | 284.160 | 412.255 | 540.350 |
| a-18  | 83.097  | 154.134 | 283.176 | 411.271 | 539.366 |
| b     | 129.102 | 200.139 | 329.182 | 457.277 | 585.372 |
| b-17  | 112.076 | 183.113 | 312.155 | 440.250 | 568.345 |
| b-18  | 111.092 | 182.129 | 311.171 | 439.266 | 567.361 |
| b+18  | 147.113 | 218.150 | 347.193 | 475.287 | 603.382 |
| c     | 146.129 | 217.166 | 346.208 | 474.303 | 602.398 |
| x     | 173.092 | 301.187 | 430.230 | 501.267 | 629.362 |
| y     | 147.113 | 275.208 | 404.250 | 475.287 | 603.382 |
| z     | 130.086 | 258.181 | 387.224 | 458.261 | 586.356 |
| i     | 101.107 | 44.049  | 102.054 | 101.107 | 101.107 |
|       | Lys     | Lys     | Glu     | Ala     | Lys     |
|       | 5       | 4       | 3       | 2       | 1       |

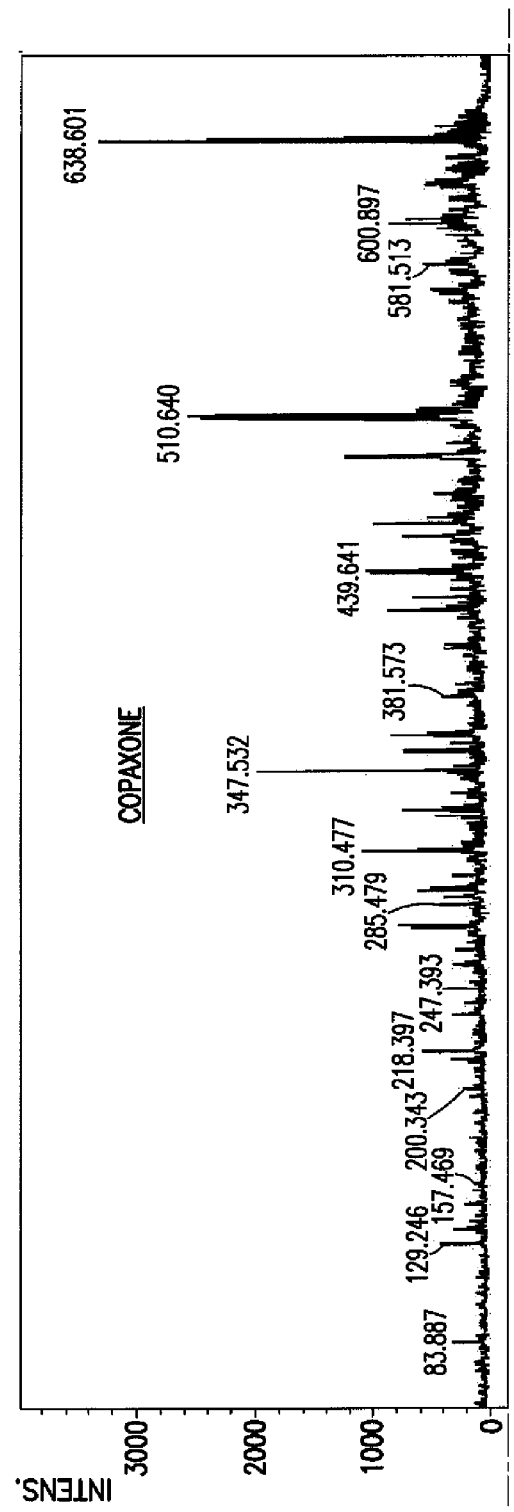

| Ion | K | A | E | K | K | Lys | Ala | Glu | Lys | Lys |
|---|---|---|---|---|---|---|---|---|---|---|
| | 1 | 2 | 3 | 4 | 5 | 1 | 2 | 3 | 4 | 5 |
| a | K | A | E | K | K | 101.107 | 172.144 | 301.187 | 464.250 | 592.345 |
| a-17 | K | A | E | K | K | 84.081 | 155.118 | 284.160 | 447.224 | 575.319 |
| a-18 | K | A | E | K | K | 83.097 | 154.134 | 283.176 | 446.240 | 574.335 |
| b | K | A | E | K | K | 129.102 | 200.139 | 329.182 | 492.245 | 620.340 |
| b-17 | K | A | E | K | K | 112.076 | 183.113 | 312.155 | 475.219 | 603.314 |
| b-18 | K | A | E | K | K | 111.092 | 182.129 | 311.171 | 474.235 | 602.330 |
| b+18 | K | A | E | K | K | 147.113 | 218.150 | 347.193 | 510.256 | 638.351 |
| c | K | A | E | K | K | 146.129 | 217.166 | 346.208 | 509.272 | 637.367 |
| x | K | A | E | K | K | 173.092 | 336.155 | 465.198 | 536.235 | 664.330 |
| y | K | A | E | K | K | 147.113 | 310.176 | 439.219 | 510.256 | 638.351 |
| z | K | A | E | K | K | 130.086 | 293.150 | 422.192 | 493.229 | 621.324 |
| i | K | A | E | K | K | 101.107 | 44.049 | 102.054 | 136.075 | 101.107 |
| | 5 | 4 | 3 | 2 | 1 | Lys | Tyr | Glu | Ala | Lys |

FIG.5b-1B

| FIG.5b-1A | FIG.5b-1B |
|---|---|

FIG.5b-1

| Ion | K | A | E | Y | K | Lys | Ala | Glu | Lys | Lys |
|---|---|---|---|---|---|---|---|---|---|---|
| | 1 | 2 | 3 | 4 | 5 | 1 | 2 | 3 | 4 | 5 |
| a | K | A | E | Y | K | 101.107 | 172.144 | 301.187 | 464.250 | 592.345 |
| a-17 | K | A | E | Y | K | 84.081 | 155.118 | 284.160 | 447.224 | 575.319 |
| a-18 | K | A | E | Y | K | 83.097 | 154.134 | 283.176 | 446.240 | 574.335 |
| b | K | A | E | Y | K | 129.102 | 200.139 | 329.182 | 492.245 | 620.340 |
| b-17 | K | A | E | Y | K | 112.076 | 183.113 | 312.155 | 475.219 | 603.314 |
| b-18 | K | A | E | Y | K | 111.092 | 182.129 | 311.171 | 474.235 | 602.330 |
| b+18 | K | A | E | Y | K | 147.113 | 218.150 | 347.193 | 510.256 | 638.351 |
| c | K | A | E | Y | K | 146.129 | 217.166 | 346.208 | 509.272 | 637.367 |
| x | K | A | E | Y | K | 173.092 | 336.155 | 465.198 | 536.235 | 664.330 |
| y | K | A | E | YY | K | 147.113 | 310.176 | 439.219 | 510.256 | 638.351 |
| z | K | A | E | Y | K | 130.086 | 293.150 | 422.192 | 493.229 | 621.324 |
| i | K | A | E | Y | K | 101.107 | 44.049 | 102.054 | 136.075 | 101.107 |
| | 5 | 4 | 3 | 2 | 1 | Lys | Tyr | Glu | Ala | Lys |

FIG.5b-2B

| FIG.5b-2A |
|---|
| FIG.5b-2B |

FIG.5b-2

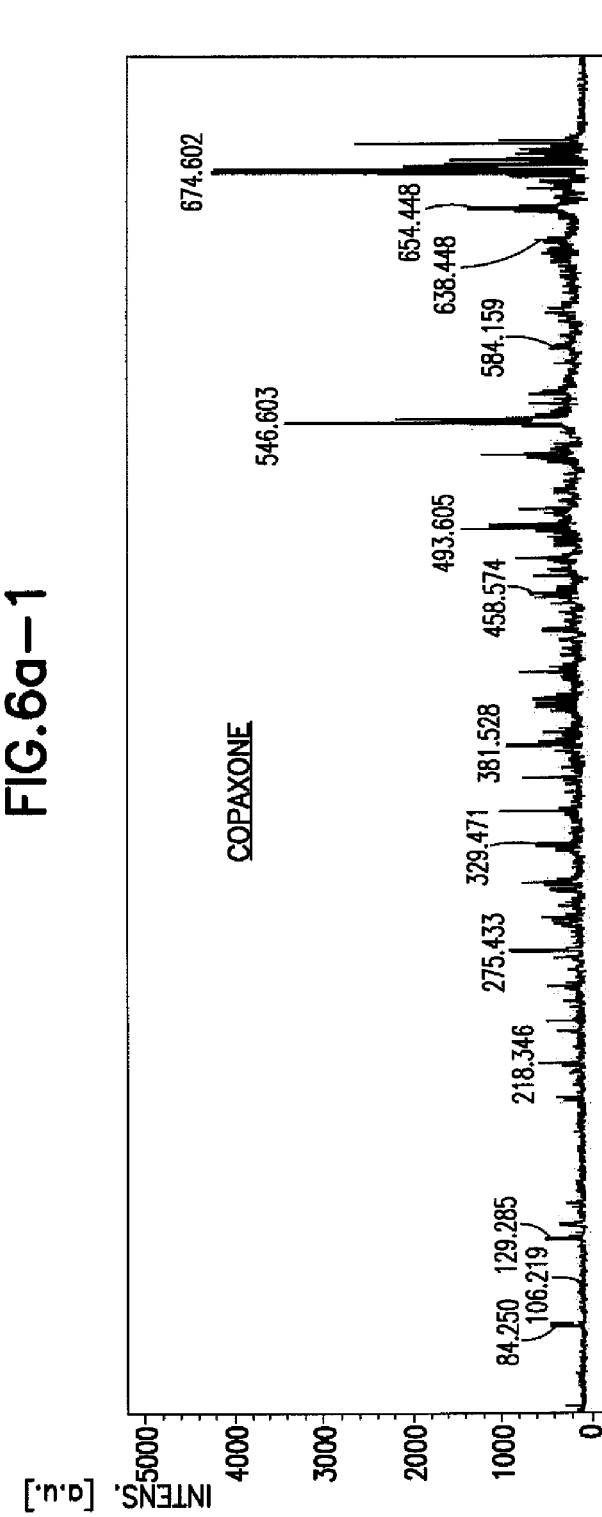

| Ion | K 1 | A 2 | E 3 | A 4 | K 5 | K 6 | Lys 1 | Ala 2 | Glu 3 | Ala 4 | Lys 5 | Lys 6 |
|---|---|---|---|---|---|---|---|---|---|---|---|---|
| a |  |  |  |  |  |  | 101.107 | 172.144 | 301.187 | 372.224 | 500.319 | 628.414 |
| a-17 |  |  |  |  |  |  | 84.081 | 155.118 | 284.160 | 355.198 | 483.293 | 611.388 |
| a-18 |  |  |  |  |  |  | 83.097 | 154.134 | 283.176 | 354.214 | 482.309 | 610.404 |
| b |  |  |  |  |  |  | 129.102 | 200.139 | 329.182 | 400.219 | 528.314 | 656.409 |
| b-17 |  |  |  |  |  |  | 112.076 | 183.113 | 312.155 | 383.193 | 511.287 | 639.382 |
| b-18 |  |  |  |  |  |  | 111.092 | 182.129 | 311.171 | 382.208 | 510.303 | 638.398 |
| b+18 |  |  |  |  |  |  | 147.113 | 218.150 | 347.193 | 418.230 | 546.325 | 674.420 |
| c |  |  |  |  |  |  | 146.129 | 217.166 | 346.208 | 417.246 | 545.341 | 673.436 |
| x |  |  |  |  |  |  | 173.092 | 301.187 | 372.224 | 501.267 | 572.304 | 700.399 |
| y |  |  |  |  |  |  | 147.113 | 275.208 | 346.245 | 475.287 | 546.325 | 674.420 |
| z |  |  |  |  |  |  | 130.086 | 258.181 | 329.218 | 458.261 | 529.298 | 657.393 |
| i |  |  |  |  |  |  | 101.107 | 44.049 | 102.054 | 44.049 | 101.107 | 101.107 |
|  |  |  |  |  |  |  | Lys | Lys | Ala | Glu | Ala | Lys |
|  |  |  |  |  |  |  | 6 | 5 | 4 | 3 | 2 | 1 |

FIG.6b-1B

| FIG.6b-1A | FIG.6b-1B |
|---|---|

FIG.6b-1

| Ion | | | | | | | Lys 1 | Ala 2 | Glu 3 | Ala 4 | Lys 5 | Lys 6 |
|---|---|---|---|---|---|---|---|---|---|---|---|---|
| | K | A | E | A | K | K | | | | | | |
| a | K | A | E | A | K | K | 101.107 | 172.144 | 301.187 | 372.224 | 500.319 | 628.414 |
| a-17 | K | A | E | A | K | K | 84.081 | 155.118 | 284.160 | 355.198 | 483.293 | 611.388 |
| a-18 | K | A | E | A | K | K | 83.097 | 154.134 | 283.176 | 354.214 | 482.309 | 610.404 |
| b | K | A | E | A | K | K | 129.102 | 200.139 | 329.182 | 400.219 | 528.314 | 656.409 |
| b-17 | K | A | E | A | K | K | 112.076 | 183.113 | 312.155 | 383.193 | 511.287 | 639.382 |
| b-18 | K | A | E | A | K | K | 111.092 | 182.129 | 311.171 | 382.208 | 510.303 | 638.398 |
| b+18 | K | A | E | A | K | K | 147.113 | 218.150 | 347.193 | 418.230 | 546.325 | 674.420 |
| c | K | A | E | A | K | K | 146.129 | 217.166 | 346.208 | 417.246 | 545.341 | 673.436 |
| x | K | A | E | A | K | K | 173.092 | 301.187 | 372.224 | 501.267 | 572.304 | 700.399 |
| y | K | A | E | A | K | K | 147.113 | 275.208 | 346.245 | 475.287 | 546.325 | 674.420 |
| z | K | A | E | A | K | K | 130.086 | 258.181 | 329.218 | 458.261 | 529.298 | 657.393 |
| i | K | A | E | A | K | K | 101.107 | 44.049 | 102.054 | 44.049 | 101.107 | 101.107 |
| | 6 | 5 | 4 | 3 | 2 | 1 | Lys | Lys | Ala | Glu | Ala | Lys |

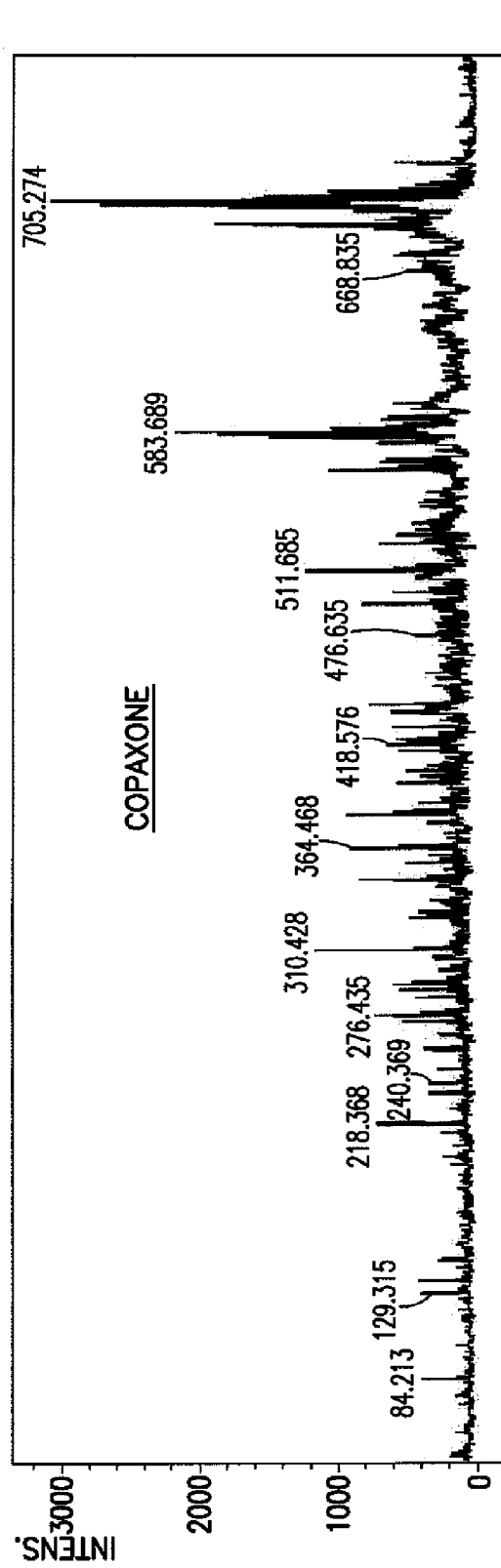

| Ion | E 1 | E 2 | A 3 | A 4 | Y 5 | K 6 | Glu 1 | Glu 2 | Ala 3 | Ala 4 | Tyr 5 | Lys 6 |
|---|---|---|---|---|---|---|---|---|---|---|---|---|
| a | E | E | A | A | Y | K | 102.055 | 231.098 | 302.135 | 373.172 | 536.235 | 664.330 |
| a-17 | E | E | A | A | Y | K | 85.028 | 214.071 | 285.108 | 356.145 | 519.209 | 647.304 |
| a-18 | E | E | A | A | Y | K | 84.044 | 213.087 | 284.124 | 355.161 | 518.225 | 646.320 |
| b | E | E | A | A | Y | K | 130.050 | 259.092 | 330.130 | 401.167 | 564.230 | 692.325 |
| b-17 | E | E | A | A | Y | K | 113.023 | 242.066 | 313.103 | 384.140 | 547.203 | 675.298 |
| b-18 | E | E | A | A | Y | K | 112.039 | 241.082 | 312.119 | 383.156 | 546.219 | 674.314 |
| b+18 | E | E | A | A | Y | K | 148.060 | 277.103 | 348.140 | 419.177 | 582.241 | 710.336 |
| c | E | E | A | A | Y | K | 147.076 | 276.119 | 347.156 | 418.193 | 581.257 | 709.352 |
| x | E | E | A | A | Y | K | 173.092 | 336.155 | 407.193 | 478.230 | 607.272 | 736.315 |
| y | E | E | A | A | Y | K | 147.113 | 310.176 | 381.213 | 452.250 | 581.293 | 710.336 |
| z | E | E | A | A | Y | K | 130.086 | 293.150 | 364.187 | 435.224 | 564.266 | 693.309 |
| i | E | E | A | A | Y | K | 102.055 | 102.054 | 44.049 | 44.049 | 136.075 | 101.107 |
|  | 6 | 5 | 4 | 3 | 2 | 1 | Lys | Tyr | Ala | Ala | Glu | Glu |

FIG.7b-1B

| | E | E | A | A | Y | K | | Glu | Glu | Ala | Ala | Tyr | Lys |
|---|---|---|---|---|---|---|---|---|---|---|---|---|---|
| Ion | 1 | 2 | 3 | 4 | 5 | 6 | | 1 | 2 | 3 | 4 | 5 | 6 |
| a | E | E | A | A | Y | K | | 102.055 | 231.098 | 302.135 | 373.172 | 536.235 | 664.330 |
| a-17 | E | E | A | A | Y | K | | 85.028 | 214.071 | 285.108 | 356.145 | 519.209 | 647.304 |
| a-18 | E | E | A | A | Y | K | | 84.044 | 213.087 | 284.124 | 355.161 | 518.225 | 646.320 |
| b | E | E | A | A | Y | K | | 130.050 | 259.092 | 330.130 | 401.167 | 564.230 | 692.325 |
| b-17 | E | E | A | A | Y | K | | 113.023 | 242.066 | 313.103 | 384.140 | 547.203 | 675.298 |
| b-18 | E | E | A | A | Y | K | | 112.039 | 241.082 | 312.119 | 383.156 | 546.219 | 674.314 |
| b+18 | E | E | A | A | Y | K | | 148.060 | 277.103 | 348.140 | 419.177 | 582.241 | 710.336 |
| c | E | E | A | A | Y | K | | 147.076 | 276.119 | 347.156 | 418.193 | 581.257 | 709.352 |
| x | E | E | A | A | Y | K | | 173.092 | 336.155 | 407.193 | 478.230 | 607.272 | 736.315 |
| y | E | E | A | A | Y | K | | 147.113 | 310.176 | 381.213 | 452.250 | 581.293 | 710.336 |
| z | E | E | A | A | Y | K | | 130.086 | 293.150 | 364.187 | 435.224 | 564.266 | 693.309 |
| i | E | E | A | A | Y | K | | 102.055 | 102.054 | 44.049 | 44.049 | 136.075 | 101.107 |
| | 6 | 5 | 4 | 3 | 2 | 1 | | Lys | Tyr | Ala | Ala | Glu | Glu |

FIG.7b-2B

| FIG.7b-2A |
|---|
| FIG.7b-2B |

FIG.7b-2

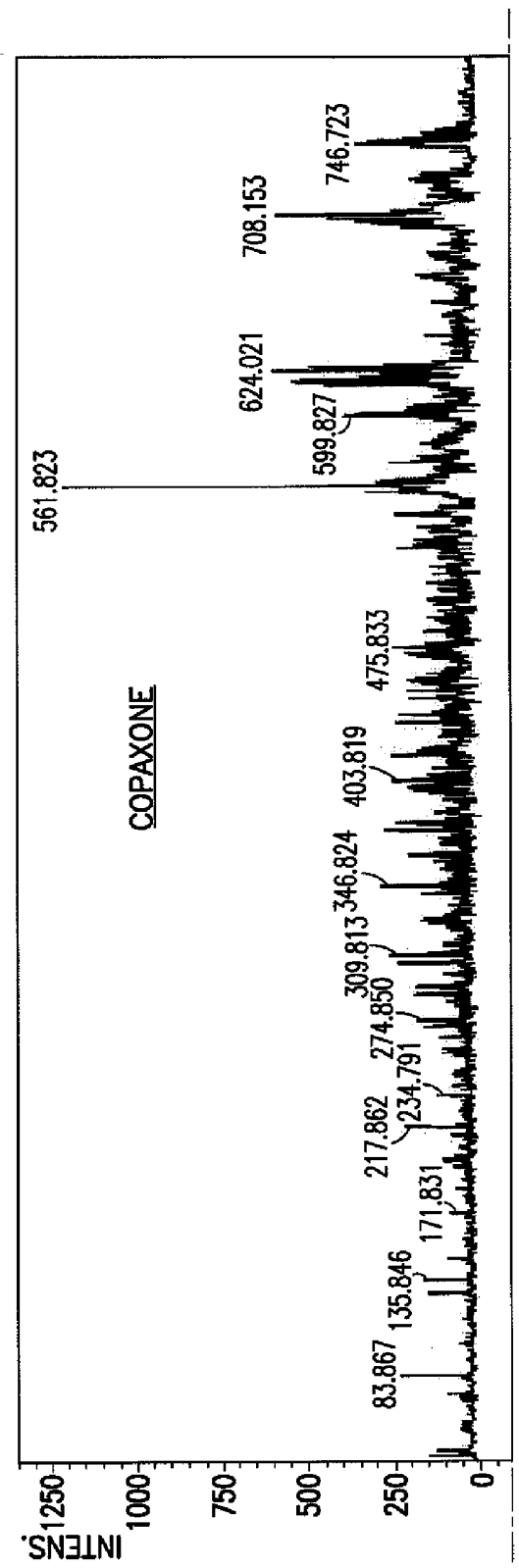

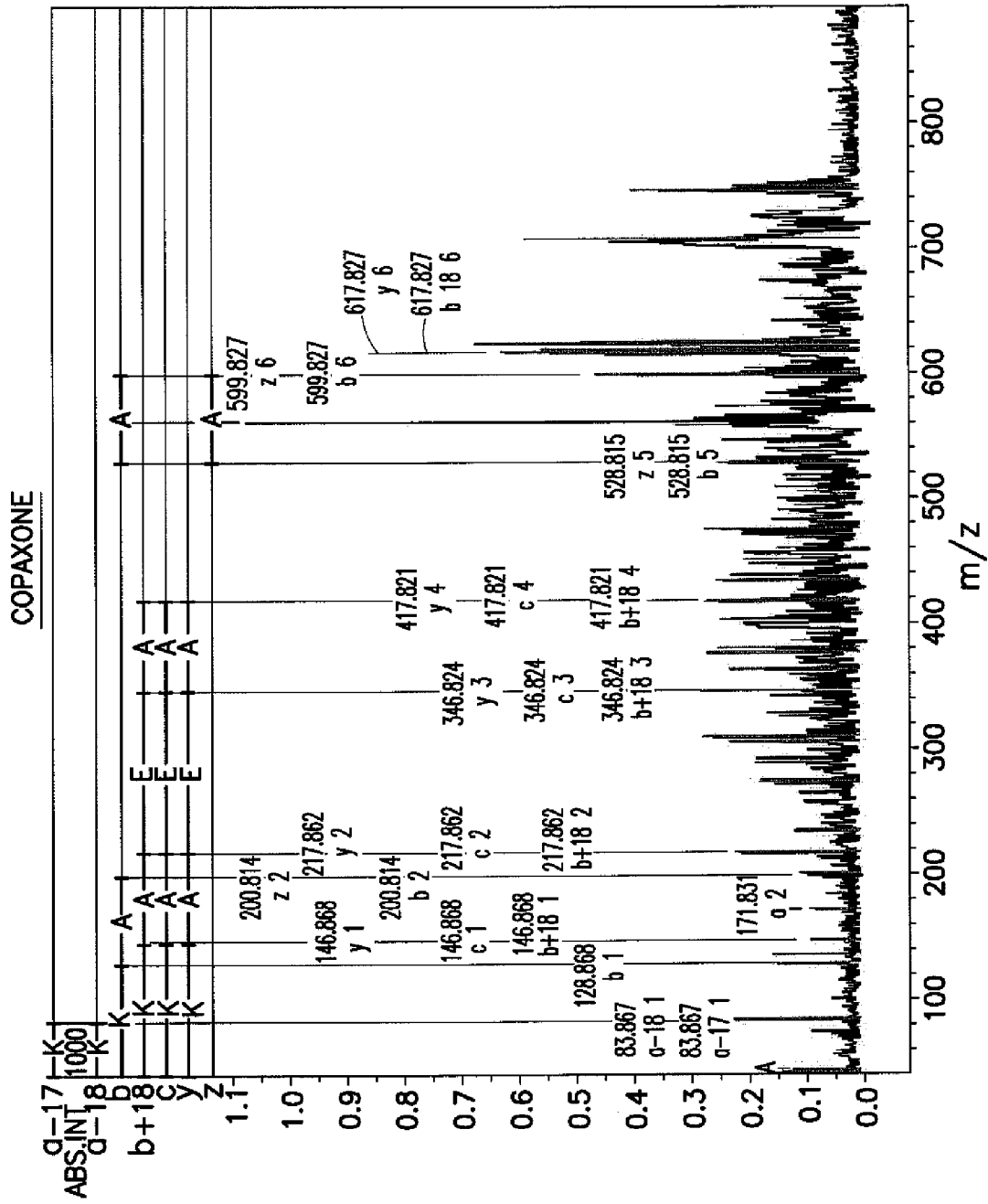

| Ion | | | | | | | | Lys 1 | Ala 2 | Glu 3 | Ala 4 | Lys 5 | Ala 6 | Lys 7 |
|---|---|---|---|---|---|---|---|---|---|---|---|---|---|---|
| | K 1 | A 2 | E 3 | A 4 | K 5 | A 6 | K 7 | | | | | | | |
| a | K | A | E | A | K | A | K | 101.107 | 172.144 | 301.187 | 372.224 | 500.319 | 571.356 | 699.451 |
| a-17 | K | A | E | A | K | A | K | 84.081 | 155.118 | 284.160 | 355.198 | 483.293 | 554.330 | 682.425 |
| a-18 | K | A | E | A | K | A | K | 83.097 | 154.134 | 283.176 | 354.214 | 482.309 | 553.346 | 681.441 |
| b | K | A | E | A | K | A | K | 129.102 | 200.139 | 329.182 | 400.219 | 528.314 | 599.351 | 727.446 |
| b-17 | K | A | E | A | K | A | K | 112.076 | 183.113 | 312.155 | 383.193 | 511.287 | 582.325 | 710.420 |
| b-18 | K | A | E | A | K | A | K | 111.092 | 182.129 | 311.171 | 382.208 | 510.303 | 581.341 | 709.436 |
| b+18 | K | A | E | A | K | A | K | 147.113 | 218.150 | 347.193 | 418.230 | 546.325 | 617.362 | 745.457 |
| c | K | A | E | A | K | A | K | 146.129 | 217.166 | 346.208 | 417.246 | 545.341 | 616.378 | 744.473 |
| x | K | A | E | A | K | A | K | 173.092 | 244.129 | 372.224 | 443.261 | 572.304 | 643.341 | 771.436 |
| y | K | A | E | A | K | A | K | 147.113 | 218.150 | 346.245 | 417.282 | 546.325 | 617.362 | 745.457 |
| z | K | A | E | A | K | A | K | 130.086 | 201.123 | 329.218 | 400.255 | 529.298 | 600.335 | 728.430 |
| i | K | A | E | A | K | A | K | 101.107 | 44.049 | 102.054 | 44.049 | 101.107 | 44.049 | 101.107 |
| | 7 | 6 | 5 | 4 | 3 | 2 | 1 | Lys | Ala | Lys | Ala | Glu | Ala | Lys |

FIG.8b-1B

| FIG.8b-1A |
|---|
| FIG.8b-1B |

FIG.8b-1

| Ion | | | | | | | | Lys 1 | Ala 2 | Glu 3 | Ala 4 | Lys 5 | Ala 6 | Lys 7 |
|---|---|---|---|---|---|---|---|---|---|---|---|---|---|---|
| | K | A | E | A | K | A | K | | | | | | | |
| | 1 | 2 | 3 | 4 | 5 | 6 | 7 | | | | | | | |
| a | K | A | E | A | K | A | K | 101.107 | 172.144 | 301.187 | 372.224 | 500.319 | 571.356 | 699.451 |
| a-17 | K | A | E | A | K | A | K | 84.081 | 155.118 | 284.160 | 355.198 | 483.293 | 554.330 | 682.425 |
| a-18 | K | A | E | A | K | A | K | 83.097 | 154.134 | 283.176 | 354.214 | 482.309 | 553.346 | 681.441 |
| b | K | A | E | A | K | A | K | 129.102 | 200.139 | 329.182 | 400.219 | 528.314 | 599.351 | 727.446 |
| b-17 | K | A | E | A | K | A | K | 112.076 | 183.113 | 312.155 | 383.193 | 511.287 | 582.325 | 710.420 |
| b-18 | K | A | E | A | K | A | K | 111.092 | 182.129 | 311.171 | 382.208 | 510.303 | 581.341 | 709.436 |
| b+18 | K | A | E | A | K | A | K | 147.113 | 218.150 | 347.193 | 418.230 | 546.325 | 617.362 | 745.457 |
| c | K | A | E | A | K | A | K | 146.129 | 217.166 | 346.208 | 417.246 | 545.341 | 616.378 | 744.473 |
| x | K | A | E | A | K | A | K | 173.092 | 244.129 | 372.224 | 443.261 | 572.304 | 643.341 | 771.436 |
| y | K | A | E | A | K | A | K | 147.113 | 218.150 | 346.245 | 417.282 | 546.325 | 617.362 | 745.457 |
| z | K | A | E | A | K | A | K | 130.086 | 201.123 | 329.218 | 400.255 | 529.298 | 600.335 | 728.430 |
| i | K | A | E | A | K | A | K | 101.107 | 44.049 | 102.054 | 44.049 | 101.107 | 44.049 | 101.107 |
| | 1 | 2 | 3 | 4 | 5 | 6 | 7 | Lys | Ala | Lys | Ala | Glu | Ala | Lys |

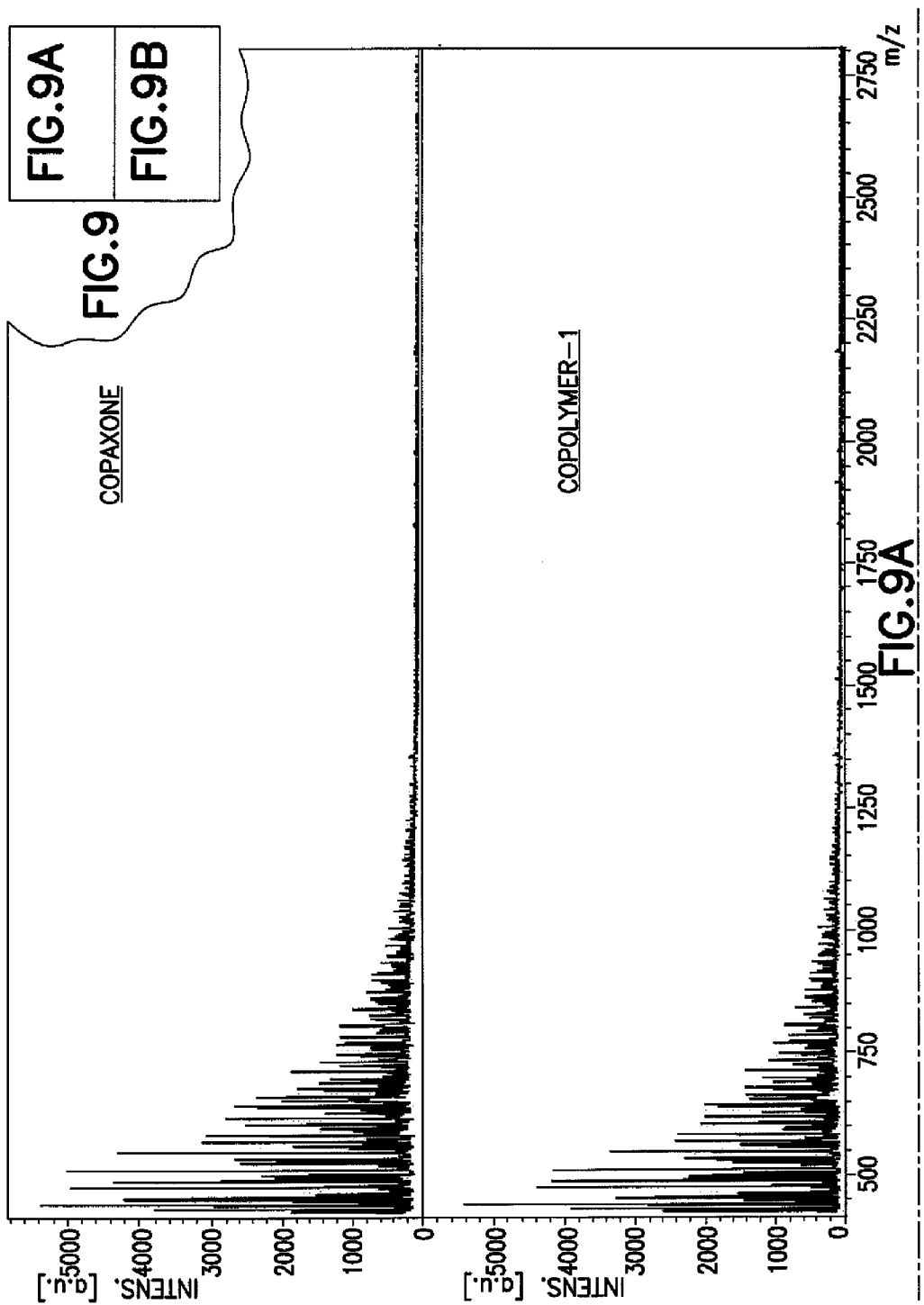

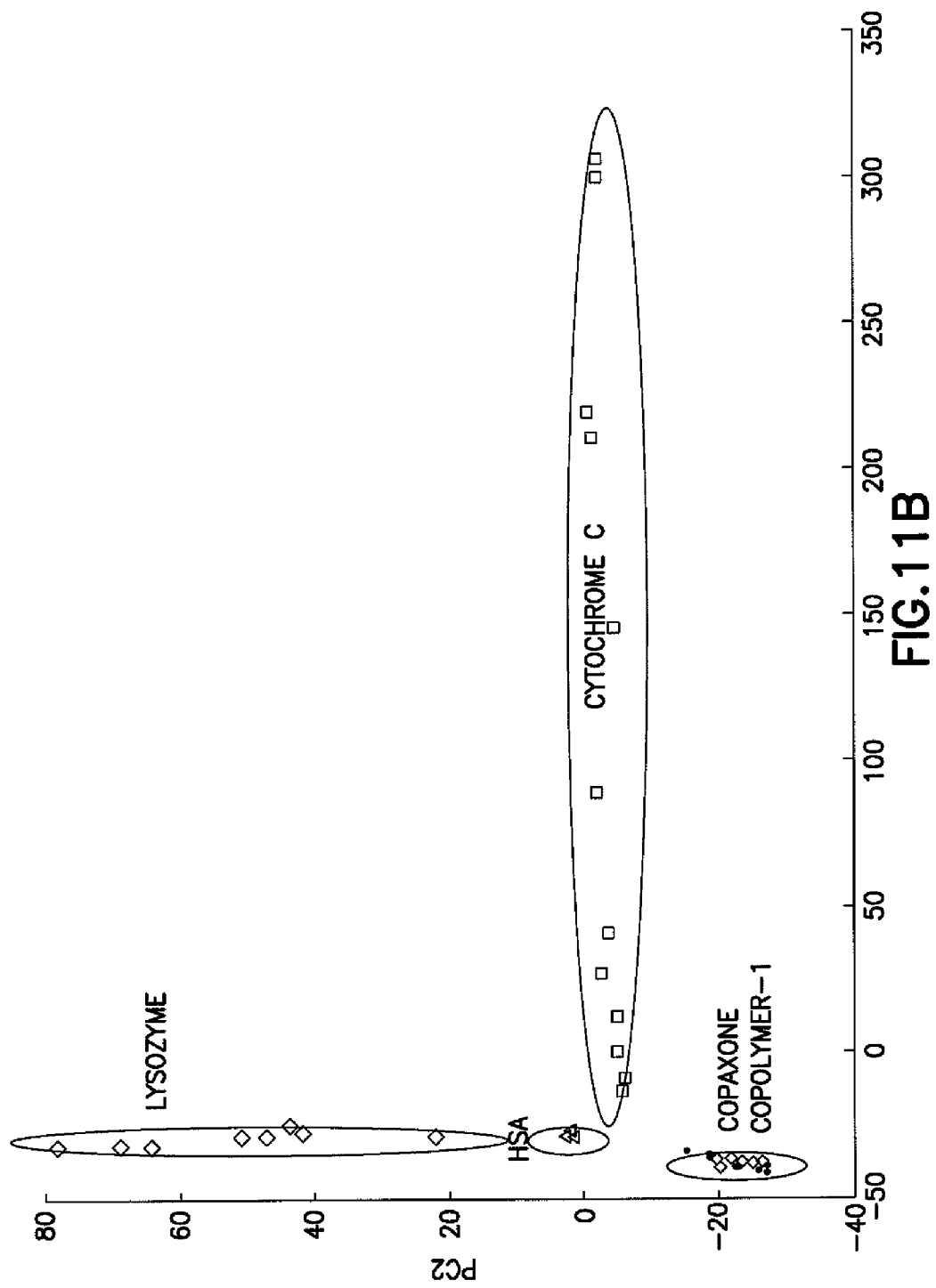

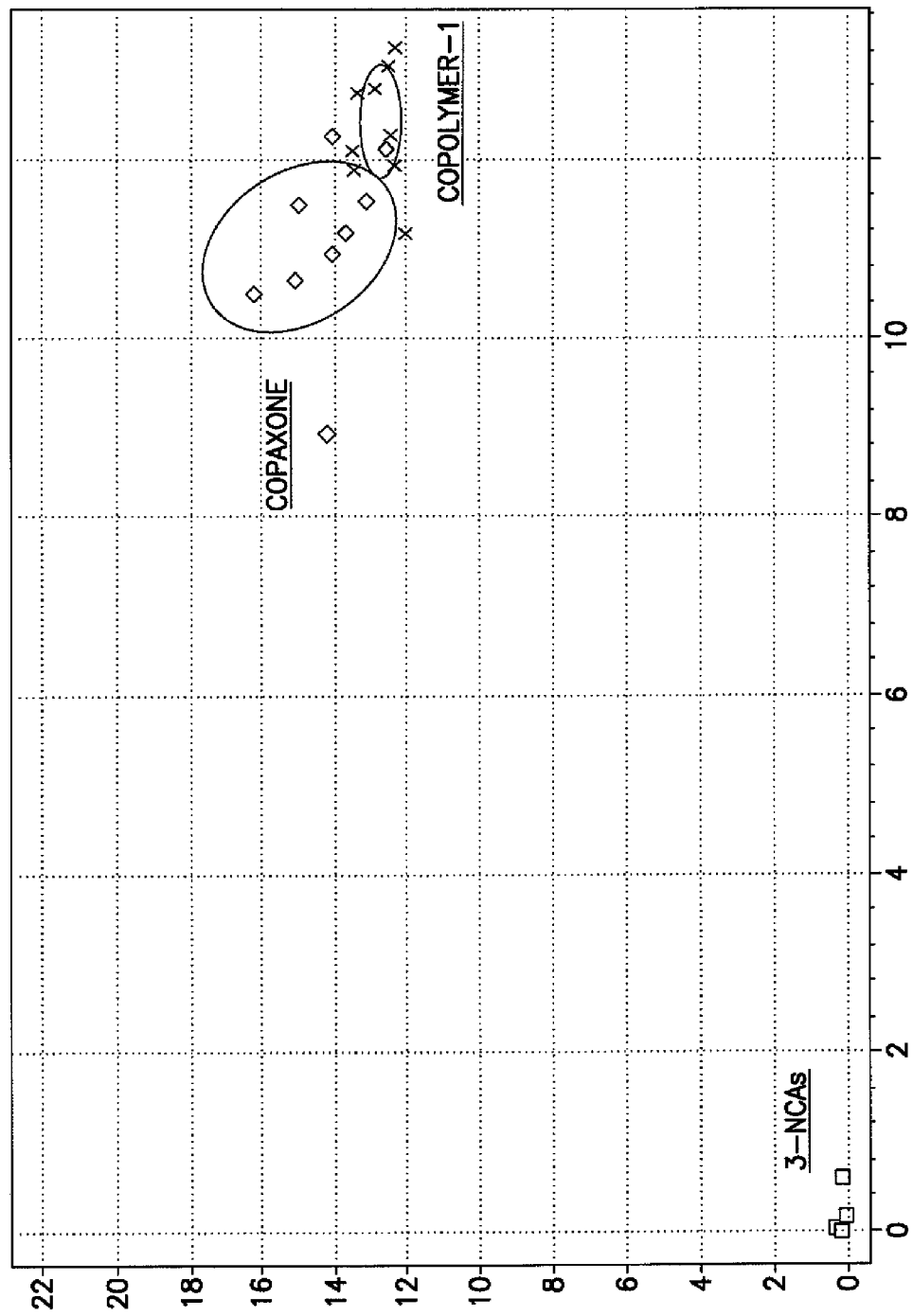

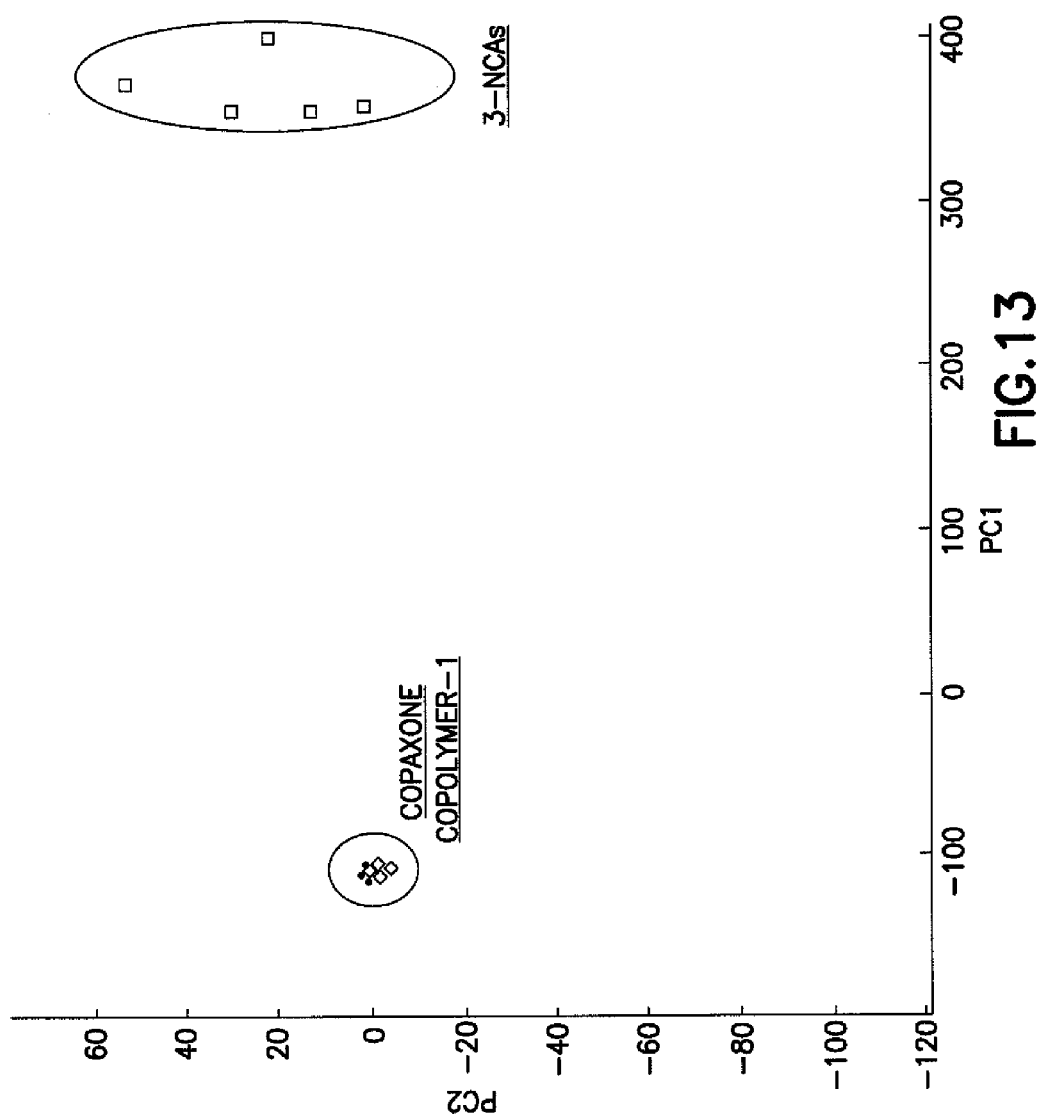

METHODS FOR CHEMICAL EQUIVALENCE IN CHARACTERIZING OF COMPLEX MOLECULES

RELATED APPLICATIONS

This application is a continuation-in-part application of U.S. patent application Ser. No. 12/775,747, filed May 7, 2010, which claims priority from U.S. Provisional Patent Application Ser. No. 61/298,367 which was filed on Jan. 26, 2010.

FIELD OF INVENTION

The present invention relates to an analytic/statistical method for characterizing, comparing, grouping and identifying complex molecules such as peptides and polypeptide mixtures, proteins and protein mixtures, and biologics, biosimilars (or called follow-on-biologics) especially monoclonal antibodies. More particularly, the present invention provides a method of characterizing samples containing such complex molecules and, more particularly, comparing reference standards and the samples based on the information obtained by characterizing the reference standards and the samples with a variety of analytic instruments. The samples may be optionally pretreated by chemical or biological digestion. The information including the signals/spectra recorded by the instruments, is analyzed by using statistical methods to assess chemical equivalence between the reference standards and the samples for grouping and identification.

BACKGROUND OF THE INVENTION

Complex molecules, such as peptides, peptide mixtures, polypeptide mixtures, proteins, protein mixtures, biologics and biosimilars (or called follow-on-biologics) especially monoclonal antibodies, are extremely difficult to characterize, group and identify in contrast to small chemical molecules. For example, small molecule drugs are typically composed of only 20 to 100 atoms; small biologics such as hormones are typically composed of 200 to 3000 atoms; while large biologics such as monoclonal antibodies are typically composed of 5,000 to 50,000 atoms.

The terms "Biosimilar" or "Follow-on-Biologic" refer to the products that are claimed to have similar structures and properties to the existing biologic products. Biosimilars are prepared and developed for market approval based on the information of existing biologic products. Due to the high complexity of some biologics, the products produced by different manufacturing processes can only be similar. It is nearly impossible to obtain the products that are exactly the same. Therefore, a powerful analytical method is required to compare, group and identify these complex products.

As generally known, the manufacturing processes for biologics are different from those for small molecule drugs. Small molecule drugs are mainly synthesized via chemical reactions. They can be well-characterized, and can be easily purified and analyzed with routine laboratory tests. The equivalence for small drug products produced by different manufacturing processes can be assessed by simple analytical methods. However, biologics, by comparison, are typically produced within specially engineered cells. Biologics, especially larger biologics, tend to be produced as diverse mixtures of molecules that differ very slightly from one another, which make them difficult to characterize. It follows that the properties of the biologics often depend directly on the nature of the manufacturing process. For example, proteins with unique structural conformation (referred to as "folding") could express different functions in the body; in addition, biologics that even have the same sequence chemically may have different biological effects due to differences in the structural folding.

One embodiment of the present invention relates to the analytic method for characterizing, comparing and classifying peptides, peptide mixtures, polypeptide mixtures and biomolecules that comprise a polypeptide component by mass spectrometry.

Copolymer-1 is a complex mixture of polypeptides prepared from the polymerization of the amino acids glutamic acid, lysine, alanine and tyrosine. Copolymer-1 also is known as glatiramer acetate and has the following structural formula:

(Glu,Ala,Lys,Tyr)$_{x \cdot x}$CH$_3$COOH

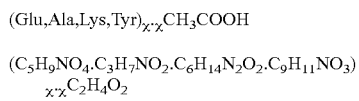

$_{x \cdot x}$C$_2$H$_4$O$_2$ (Physician Desk Reference, (2000))

Glatiramer acetate (GA) is the active ingredient of COPAXONE® (Teva Pharmaceutical Industries Ltd., Israel), which comprises the acetate salts of a synthetic polypeptide mixture containing four naturally occurring amino acids: L-glutamic acid, L-alanine, L-tyrosine, and L-lysine, with a reported average molar fraction of 0.141, 0.427, 0.095, and 0.338, respectively. The average molecular weight of COPAXONE® is between 4,700 and 11,000 daltons. Glatiramer acetate is an approved drug for the treatment of multiple sclerosis (MS). Processes for the preparation of glatiramer acetate are described in U.S. Pat. Nos. 3,849,550 and 5,800,808 and PCT International Publication No. WO 00/05250.

European Patent Application Publication No. 1 983 344 A1 discloses a method for digesting a single polypeptide standard by Trypsin and detecting its fragmentation by MADLDI-TOF. PCT International Publication No. WO 2008/135756 discloses digesting a single peptide standard by Trypsin, which provided the expected tryptic peptide fragments to be analyzed by tandem MS.

SUMMARY OF THE INVENTION

In contrast to prior art techniques, in one embodiment of the present invention, hydrolysis enzymes are used to digest a standard of a complex mixture of polypeptides, such as Glatiramer acetate, into several peptide fragments. The peptide fragments are analyzed by mass spectrometry (MS) and MS/MS. The obtained mass spectra of the digests of a sample is compared with those of other samples and served as the fingerprint of the sample.

Each peptide fragment detected by the first mass analyzer is selected and subjected to second mass spectrometric analysis (so called MS/MS analysis) to cleave the precursor peptide ions into even smaller fragments. The mass spectra obtained from MS/MS analysis are analyzed by software such as Biotools to obtain the sequence of each peptide fragment. The results reveal the compositions and sequences of peptide ions detected in the first mass analyzer. Finally, the mass spectra of the digests of the samples are analyzed with statistic software (such as ClinProTool) for classification (such as 2D peaks distribution) through univariate peak rankings obtained from statistical tests (t-test, ANOVA ... ). Grouping or distinction of different samples is also achieved by multivariate statistic (Principal Component Analysis, PCA). This strategic approach is to statistically compares the mass spectra of different products and differentiate the samples based on the resulting classification and locations of spots.

A second embodiment of the present invention provides an analytical/statistical method to characterize complex molecules generally for comparing, grouping and identifying. This embodiment provides an approach to evaluate the chemical similarities between two highly complex macromolecules. The signals/spectra recorded from a variety of analytic instruments can be applied in this invention. The analytical instruments include mass spectrometry, nuclear magnetic resonance (NMR), Raman spectroscopy, infrared spectroscopy (IR), near-Infrared spectroscopy (Near-IR), ultraviolet-visible spectroscopy (UV/Vis), circular dichroism (CD) and optical rotation dispersion (ORD). Without sample pretreatment, the signals/spectra obtained from mass spectrometry are the average results of all molecules in the sample. No differences on the signals/spectra are usually obtained between different samples. To obtain meaningful signals/spectra to reflect the differences on the composition of the complex mixtures, the sample is cut to smaller fragments by chemical reactions or biological digestions. High resolution mass spectrometry is then used to efficiently characterize the treated sample. Complex data sets are usually obtained.

Multiple variant analysis such as principal component analysis (PCA) is a simple, non-parametric method for the reduction of a complex data set to one of lower dimension, usually with the aim of revealing simplified relationships. It is a statistical analysis method and can be treated as a process model to characterize the product due to its manufacturing process or its properties. PCA involves a mathematical procedure that transforms a number of possibly correlated variables into a smaller number of uncorrelated variables called principal components. The first principal component accounts for as much of the variability in the data as possible, and each succeeding component accounts for as much of the remaining variability as possible.

The signals/spectra from a variety of analytic instruments coupled with multiple variant analysis can potentially provide meaningful comparative information of the complex molecules.

BRIEF DESCRIPTION OF THE DRAWINGS

In the drawings:

FIG. 11B: The plot of PC1 against PC2 of Copaxone, Copolymer-1, Cytochrom C, lysozyme and HSA FIG. 12: 2D peaks distribution from the first two peaks based on univariate peak ranking for mass spectra of enzyme-digested Copaxone, Copolymer-1, and 3-NCAs FIG. 13: The plot of PC1 against PC2 of Copaxone, Copolymer-1 and 3-NCAs

DETAILED DESCRIPTION OF THE INVENTION

Figure 1B:
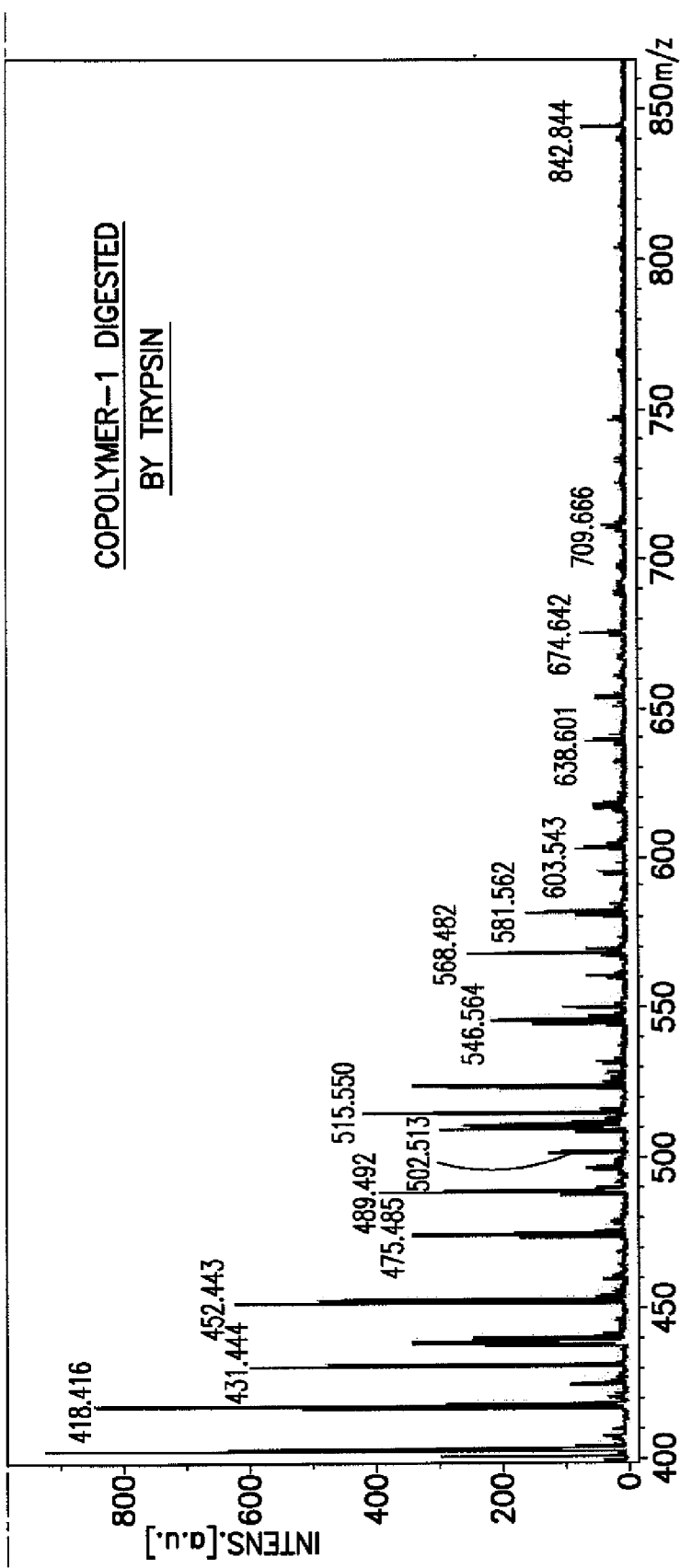
FIG. 1: Mass spectra for the comparison between enzyme-digested Copaxone (FIG. 1A) and Copolymer-1 (FIG. 1B)
Figures 2, 2A:
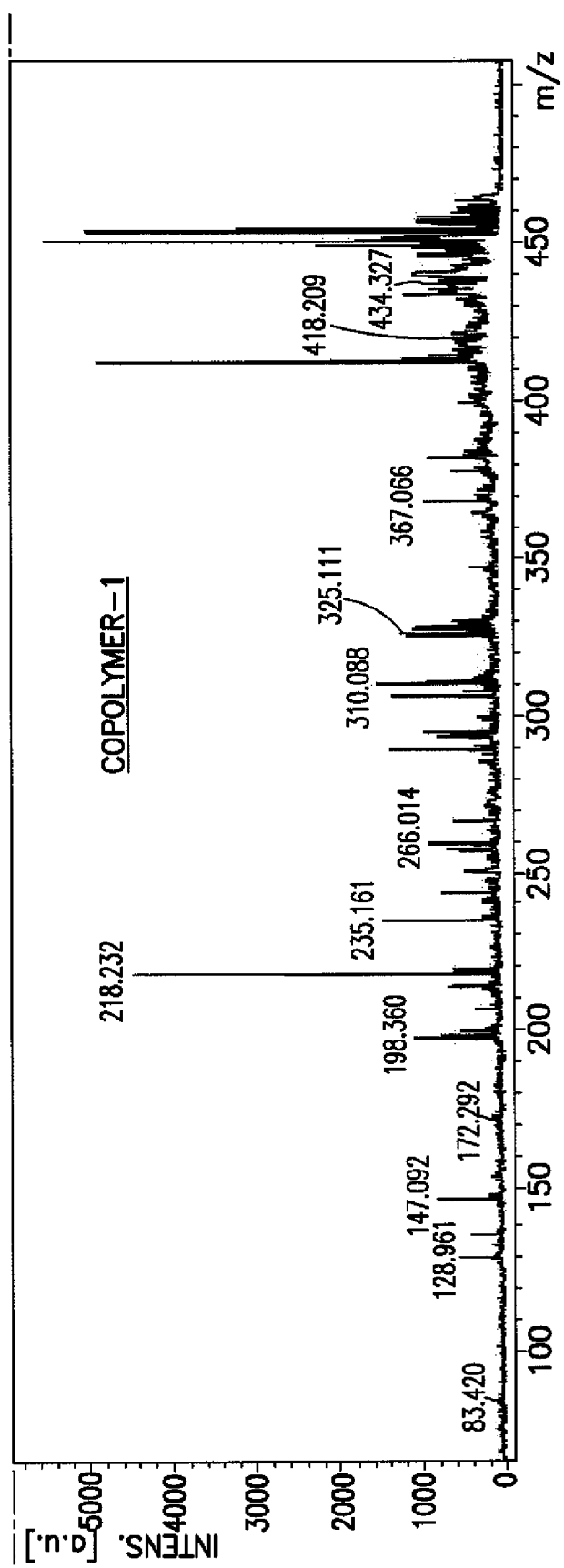
FIG. 2a: MS/MS spectra of the ion-m/z 452.44 recorded from enzyme-digested Copaxone (FIG. 2a-1) and Copolymer-1 (FIG. 2a-2)
Figures 1A, 2B:
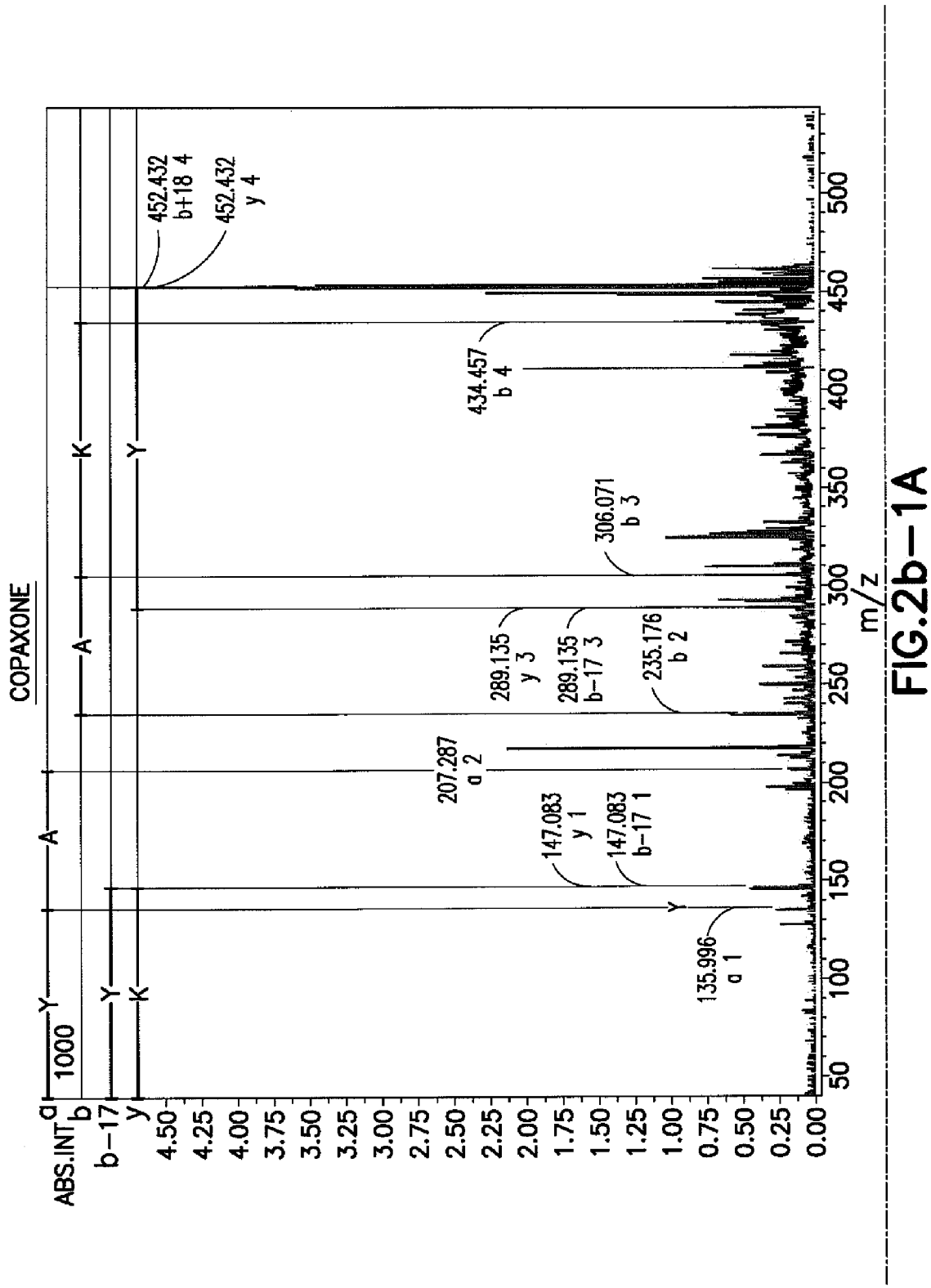
FIG. 2b: Sequence and fragment ions of m/z 452.44 for enzyme-digested Copaxone (FIG. 2b-1A and 1B) and Copolymer-1 (FIG. 2b-2A and 2B)
Figures 2A, 2B:
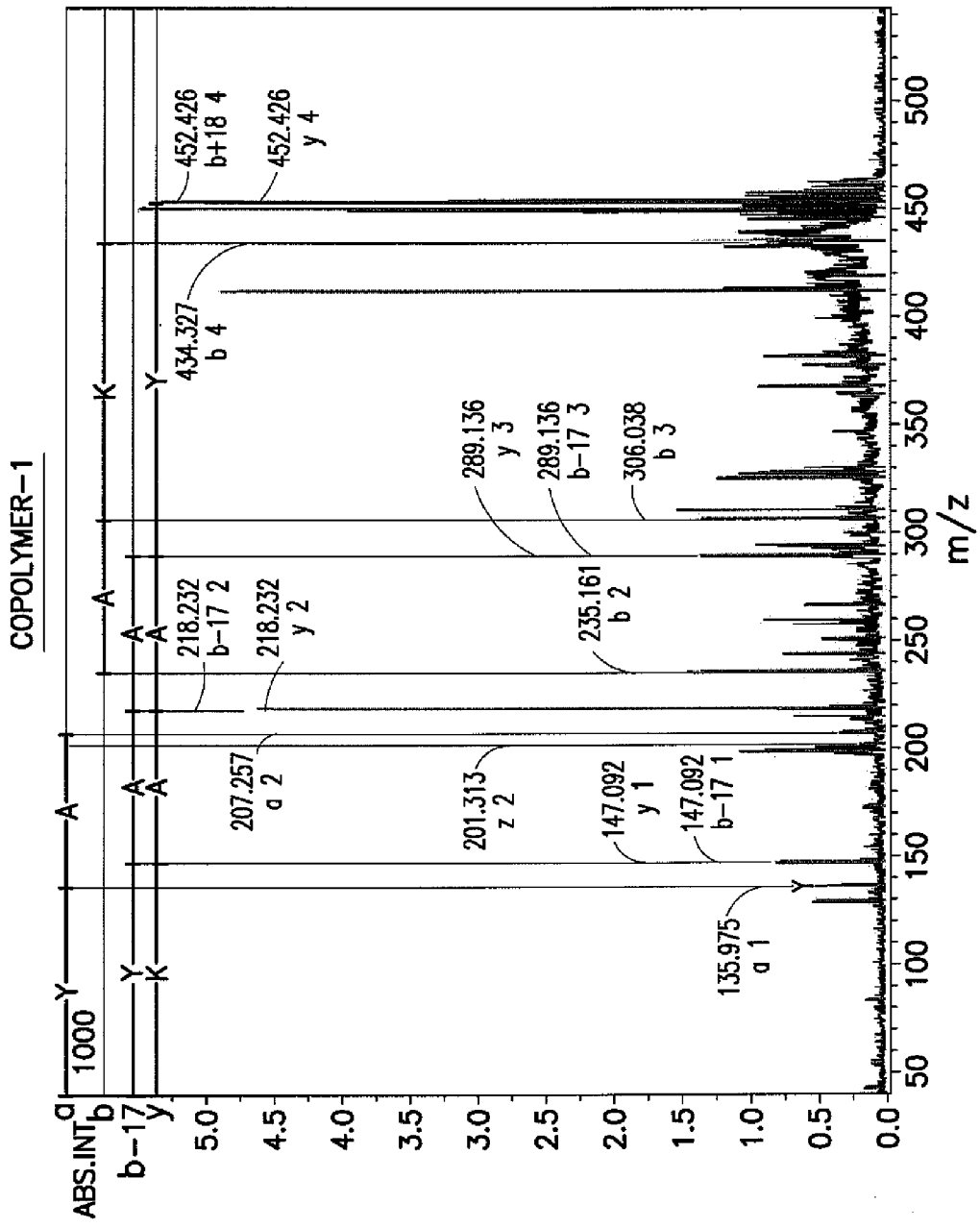
Figures 2, 3A:
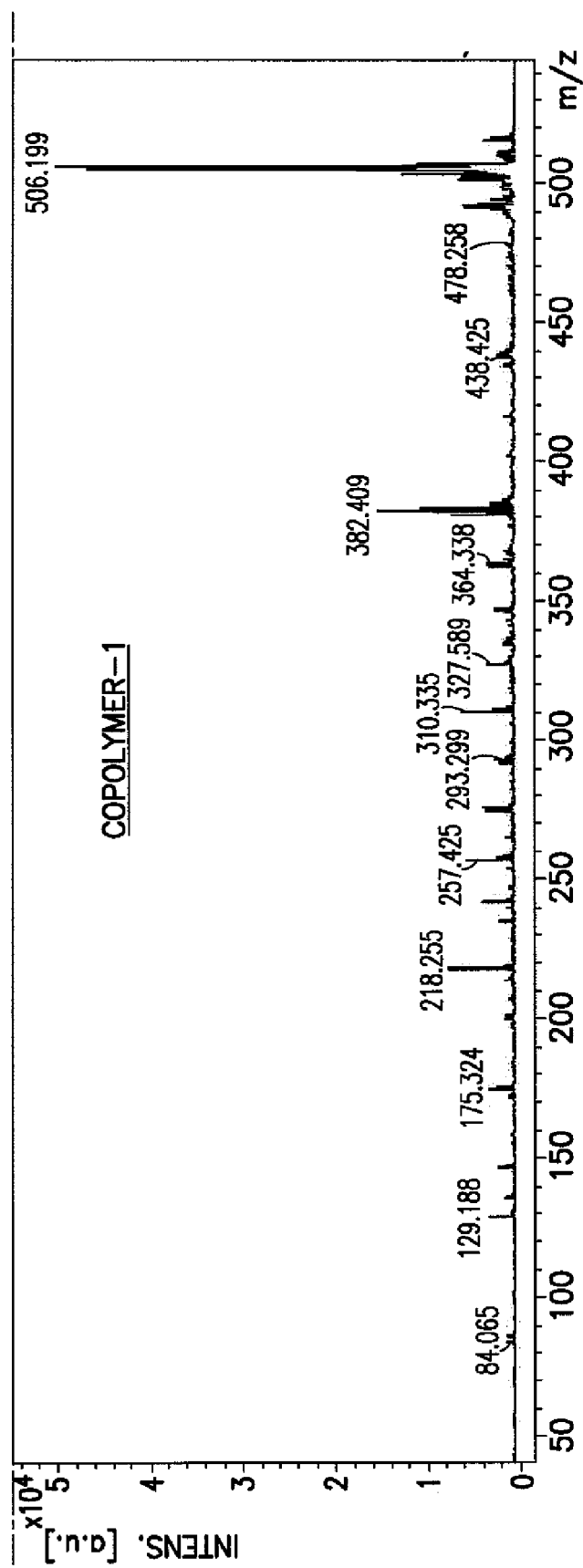
FIG. 3a: MS/MS spectra of m/z 509.385 recorded from enzyme-digested Copaxone (FIG. 3a-1) and Copolymer-1 (FIG. 3a-2)
Figures 1A, 3B:
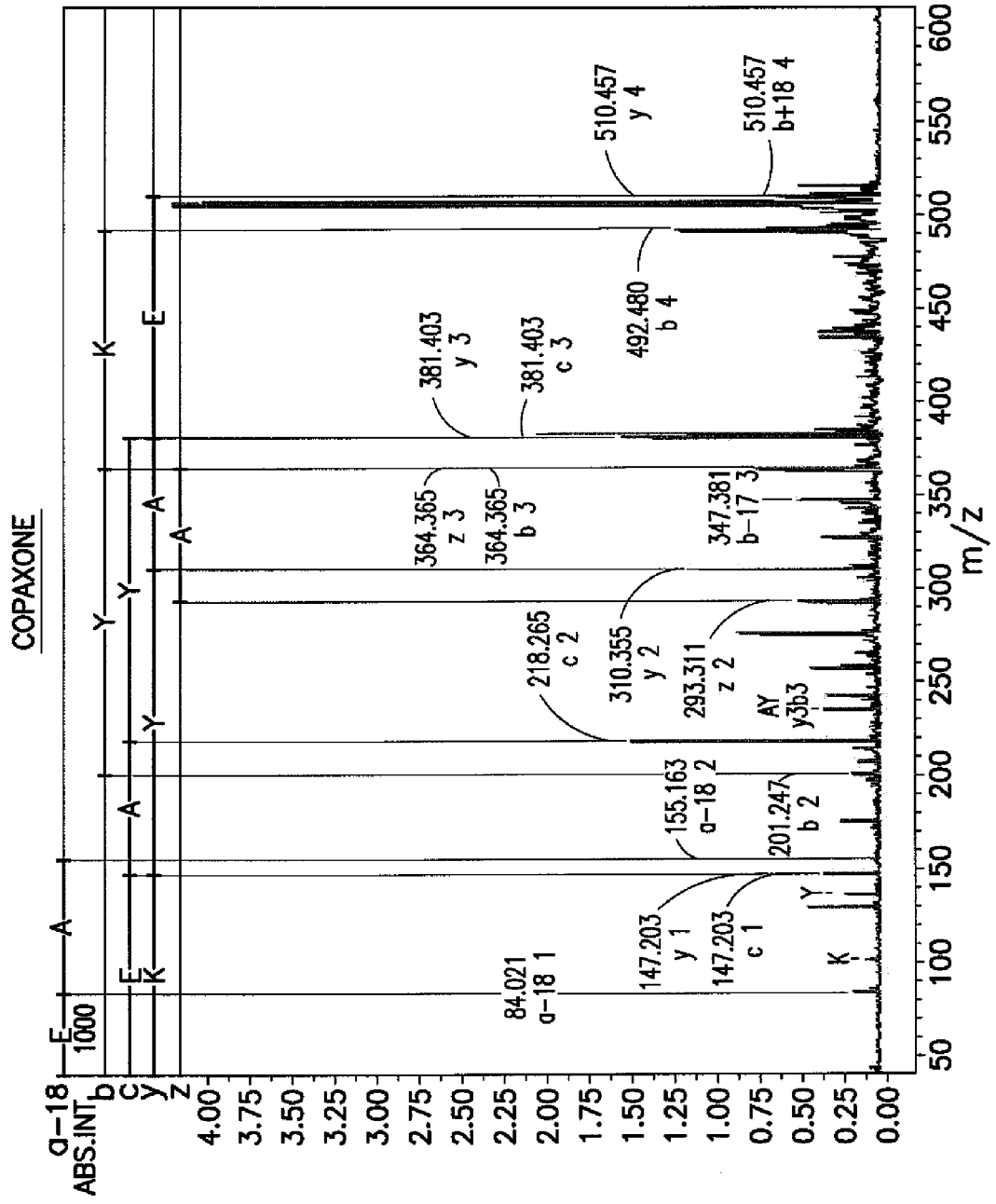
FIG. 3b: Sequence and fragment ions of m/z 509.385(1) of enzyme-digested Copaxone (FIG. 3b-1A and 1B) and Copolymer-1 (FIG. 3b-2A and 2B)
Figures 2A, 3B:
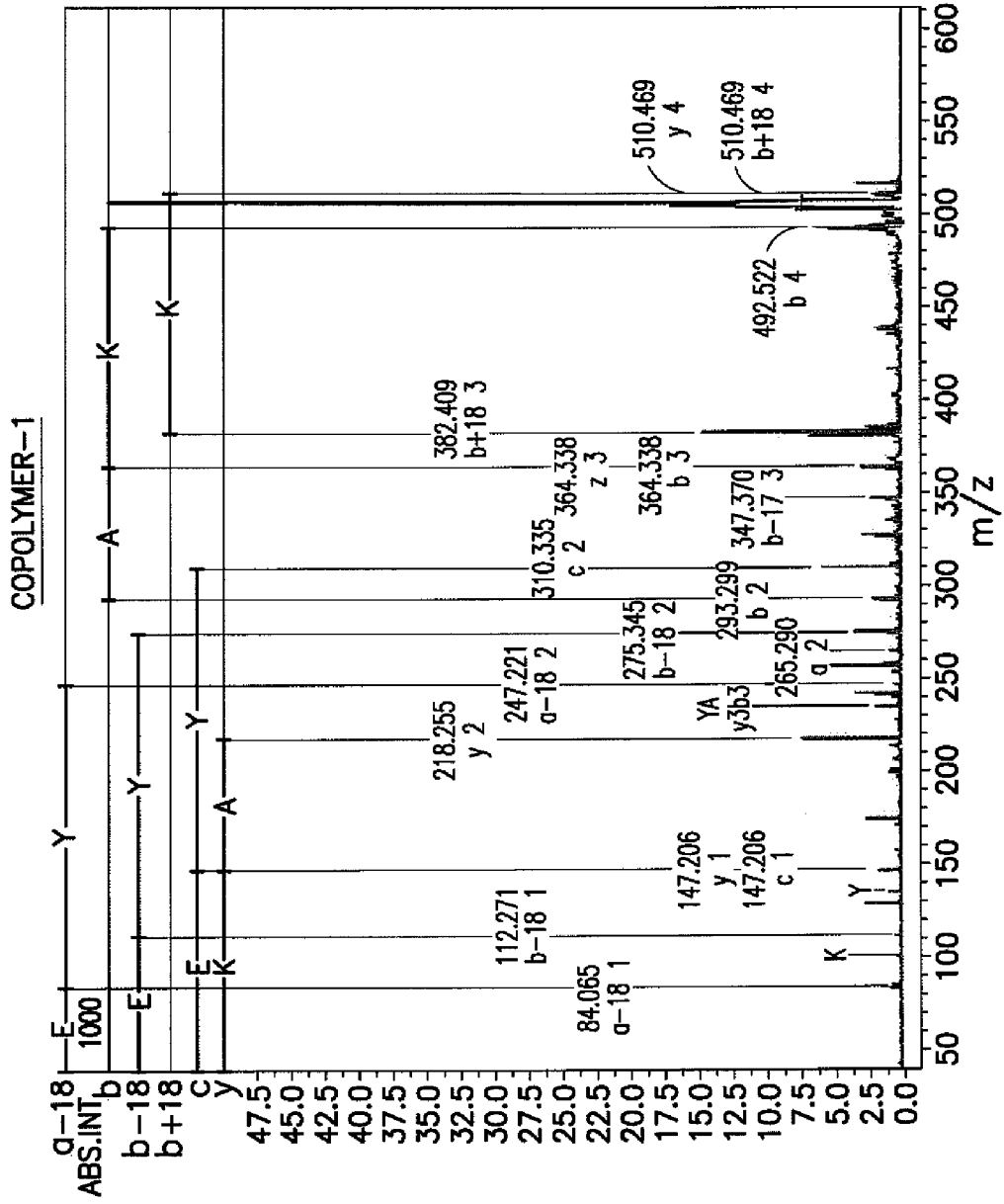
Figures 1A, 3C:
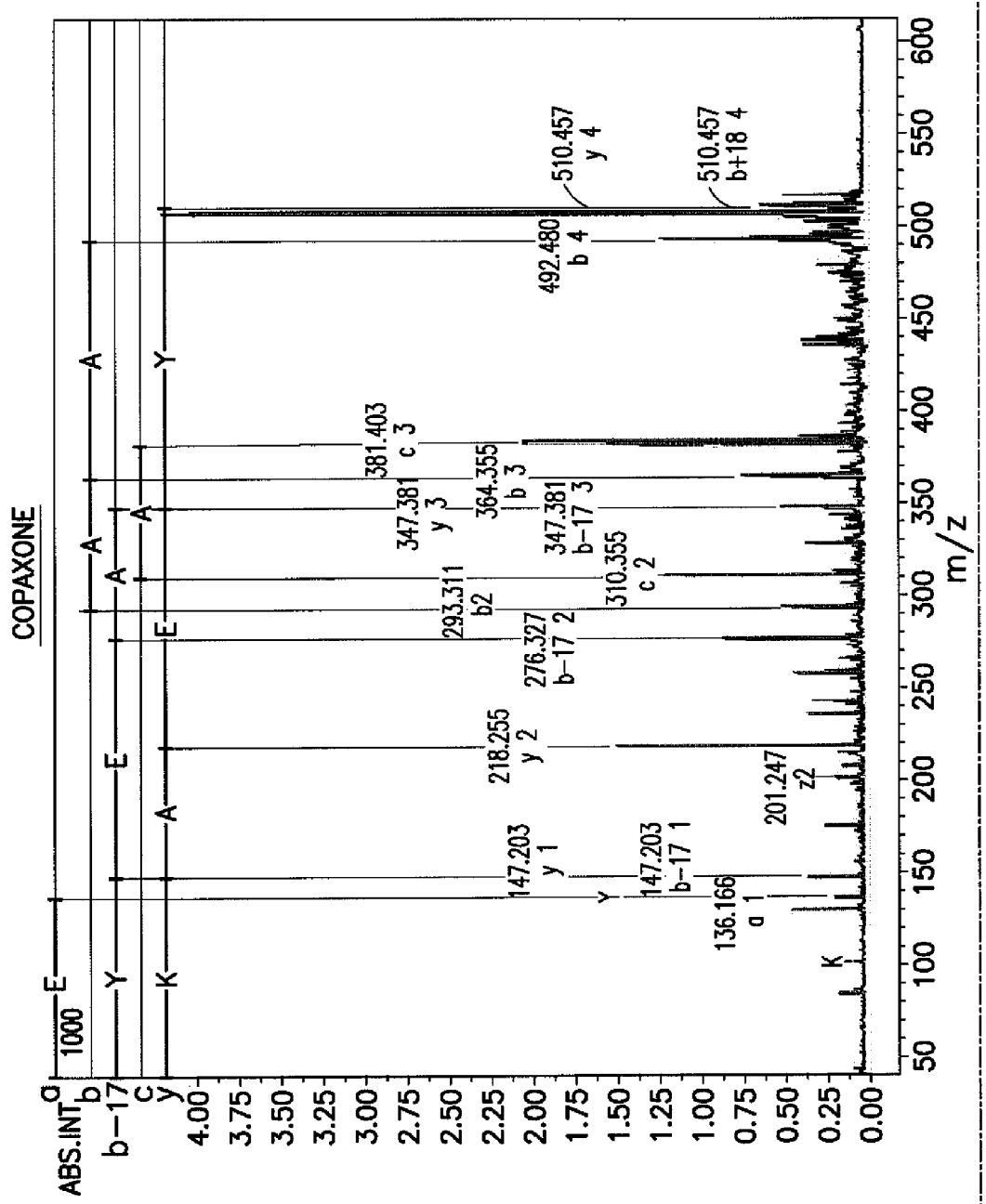
FIG. 3c: Sequence and fragment ions of m/z 509.385(2) of enzyme-digested Copaxone (FIG. 3c-1A and 1B) and Copolymer-1 (FIG. 3c-2A and 2B)
Figures 2A, 3C:
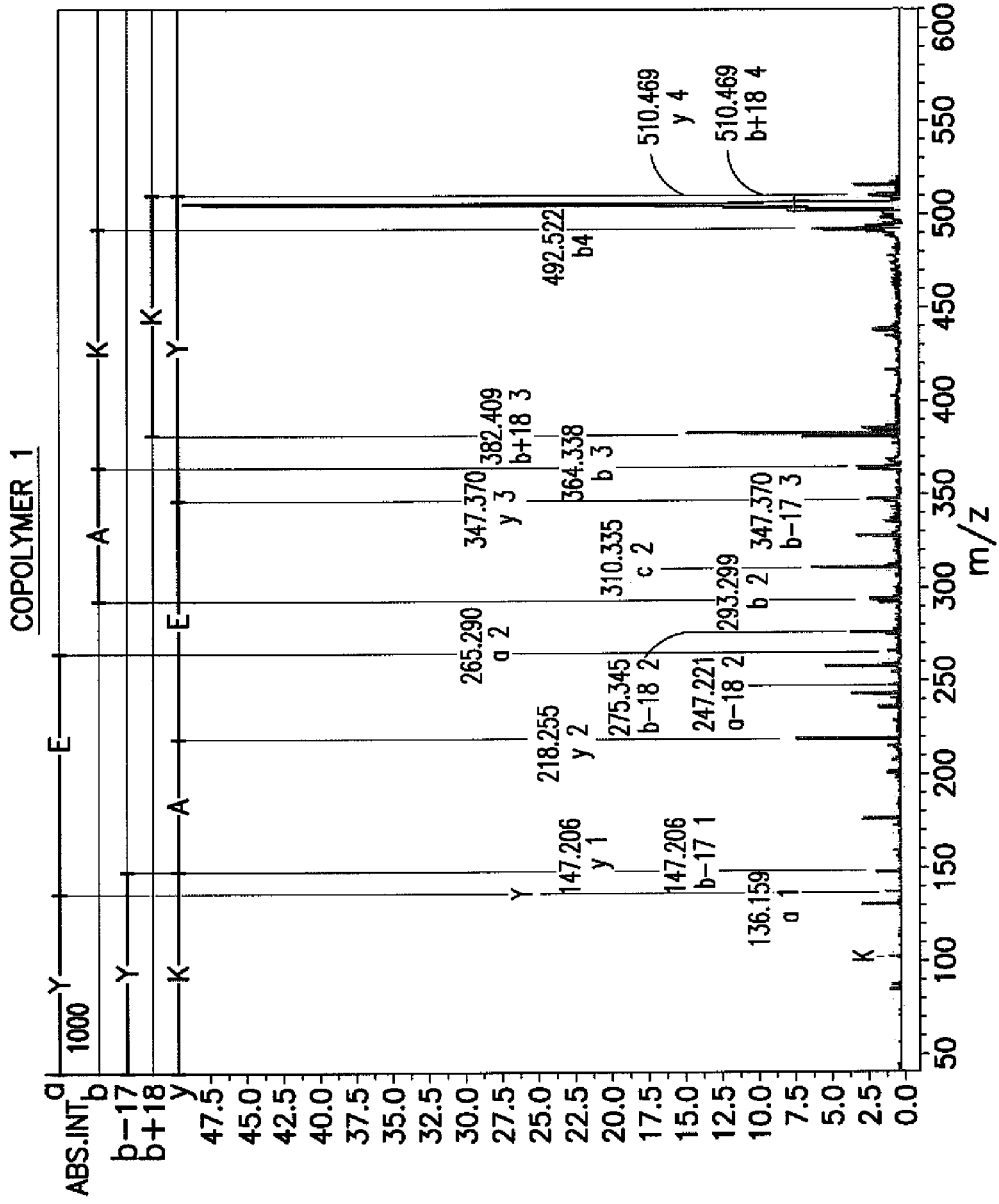
Figures 1, 4A:
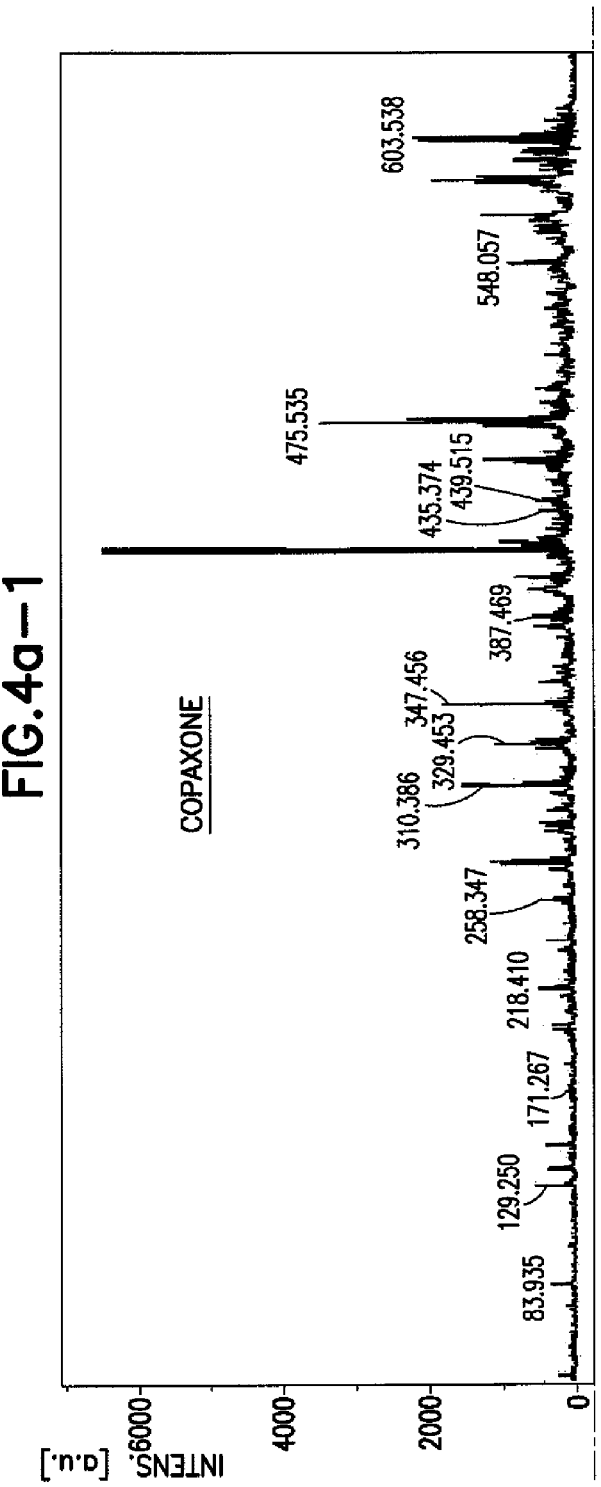
FIG. 4a: MS/MS spectra of m/z 603.515 recorded from enzyme-digested Copaxone (FIG. 4a-1) and Copolymer-1 (FIG. 4a-2)
Figures 2, 4A:
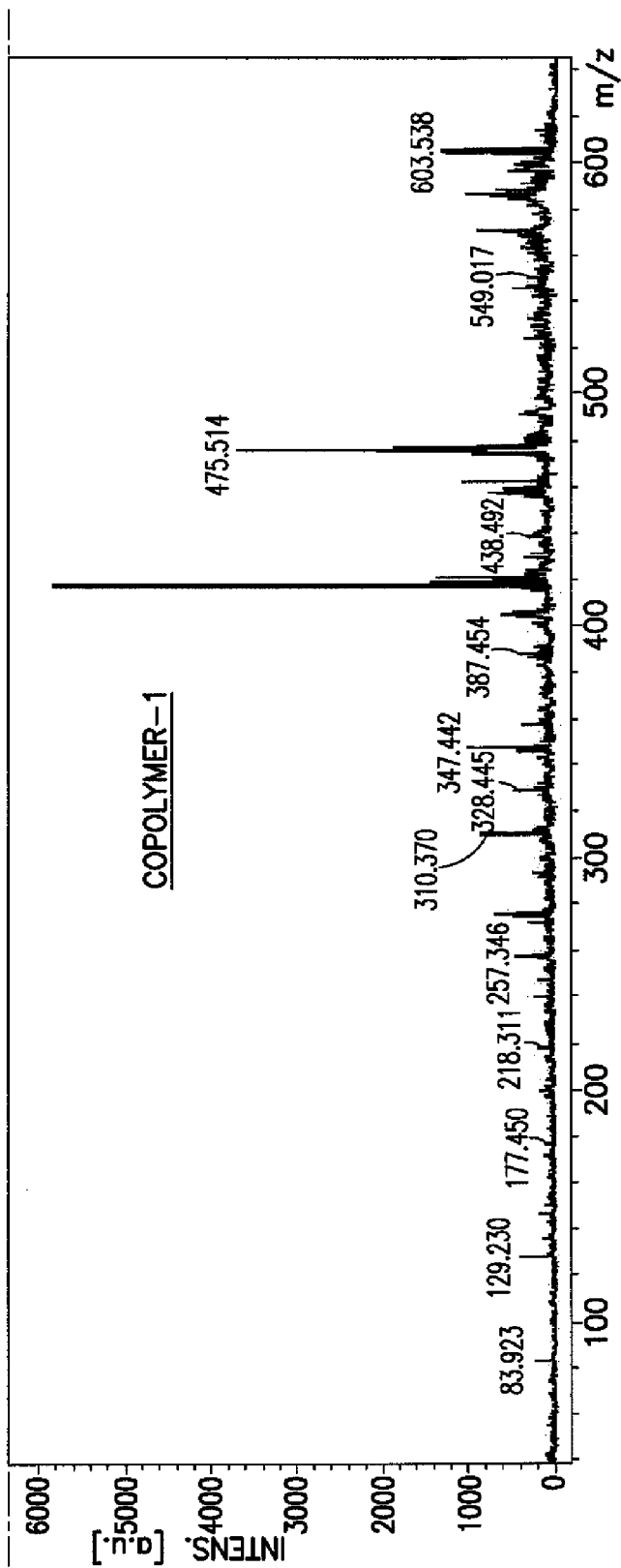
Figures 1A, 4B:
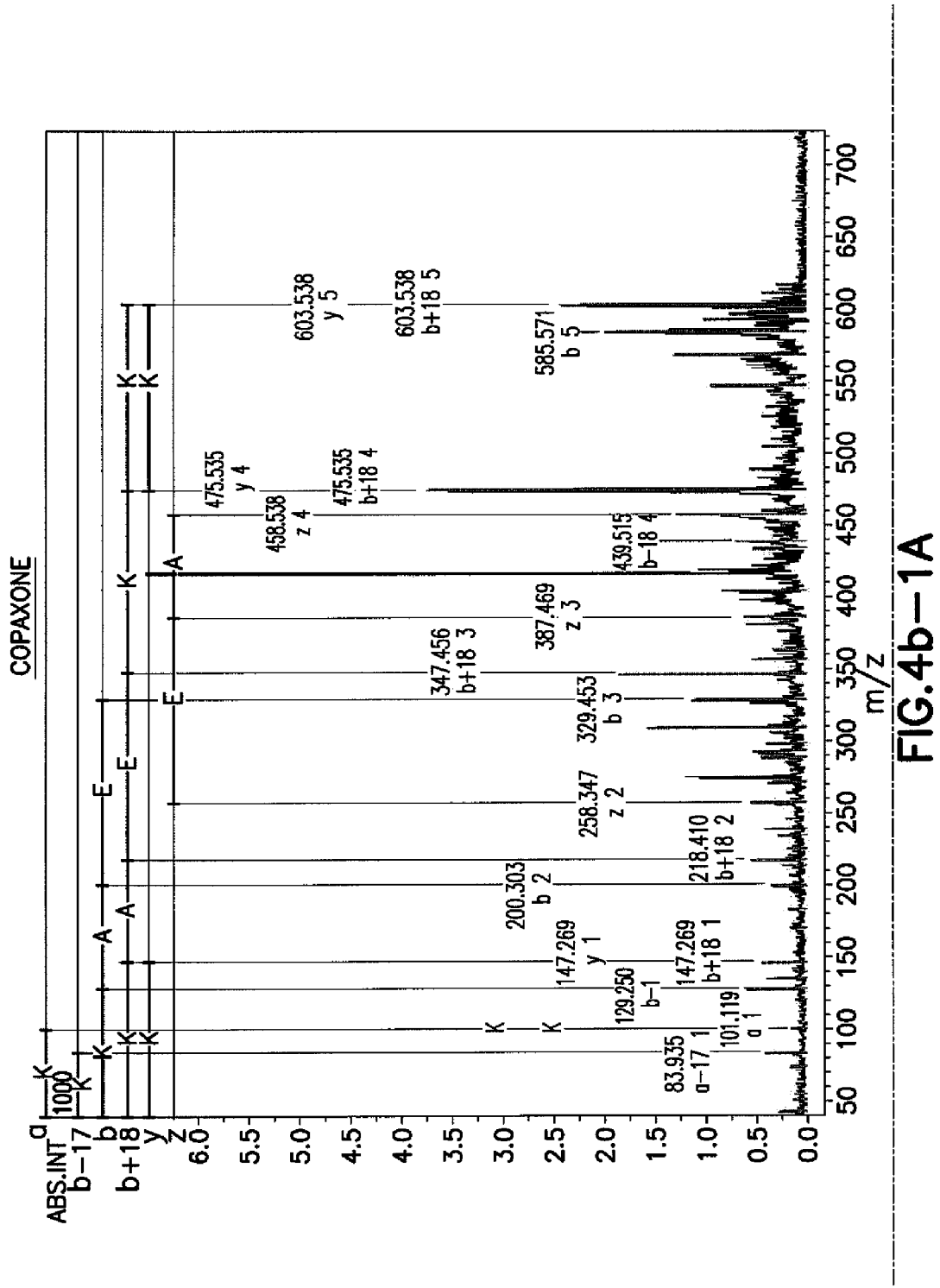
FIG. 4b: Sequence and fragment ions of m/z 603.515 of enzyme-digested Copaxone (FIG. 4b-1A and 1B) and Copolymer-1 (FIG. 4b-2A and 2B)
Figures 2A, 4B:
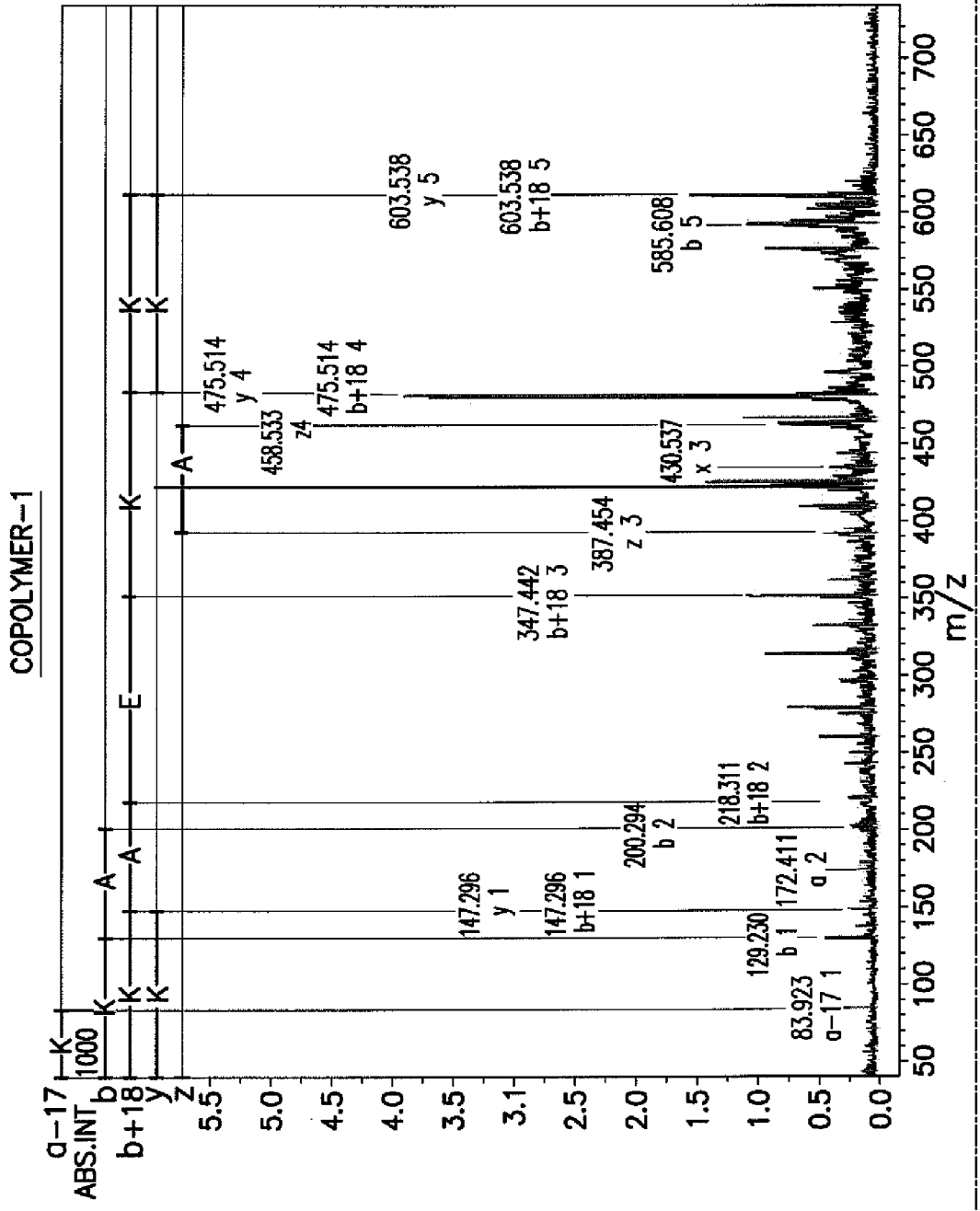
Figures 2, 5A:
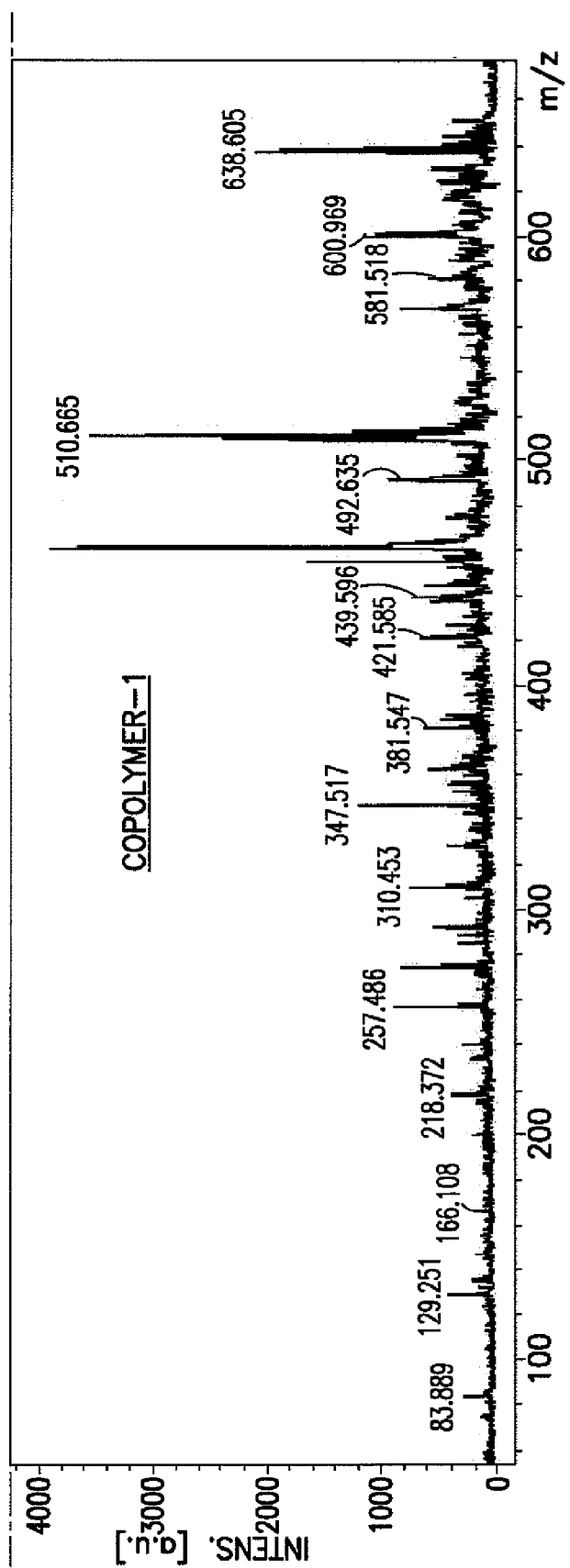
FIG. 5a: MS/MS spectra of m/z 638.590 recorded from enzyme-digested Copaxone (FIG. 5a-1) and Copolymer-1 (FIG. 5a-2)
Figures 1A, 5B:
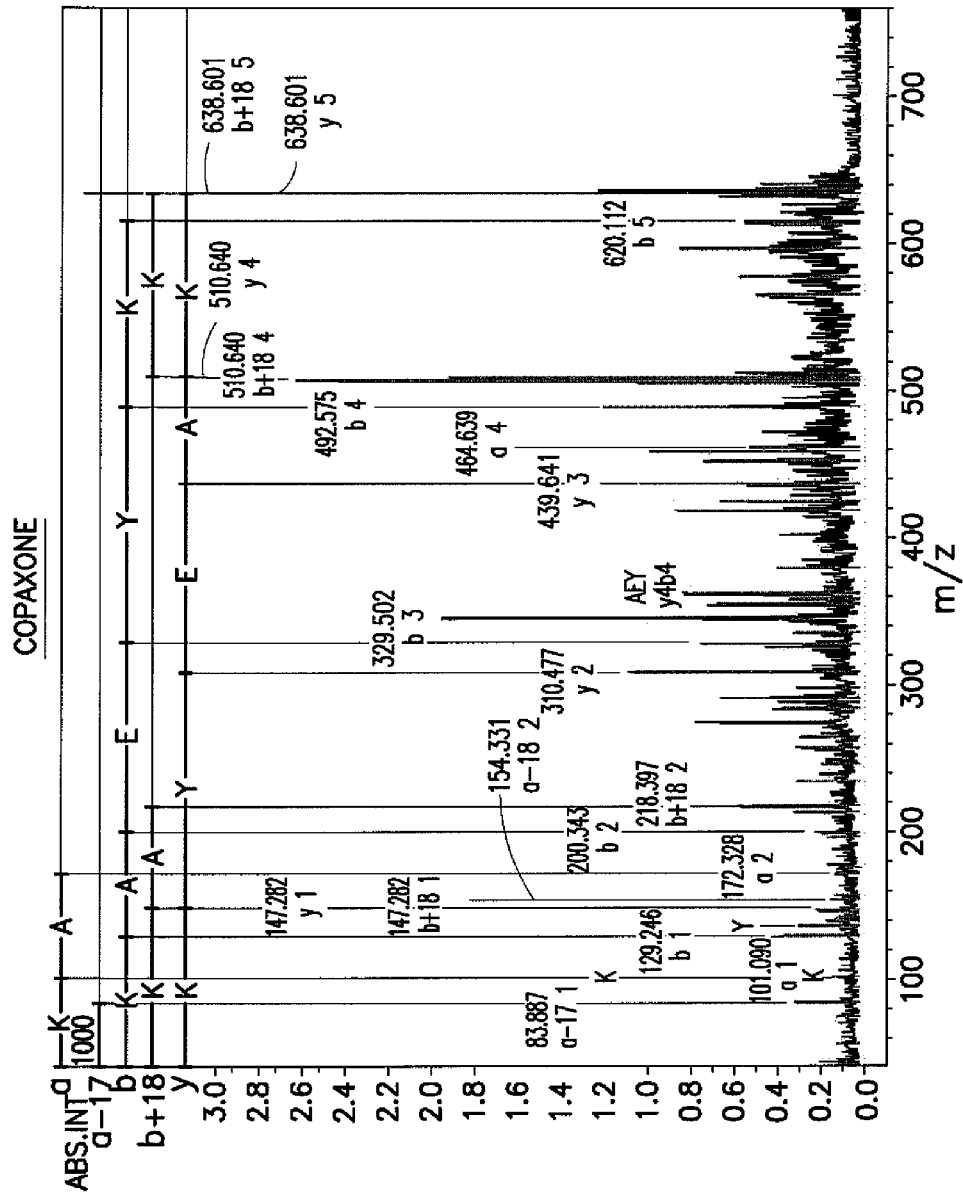
FIG. 5b: Sequence and fragment ions of m/z 638.590 of enzyme-digested Copaxone (FIG. 5b-1A and 1B) and Copolymer-1 (FIG. 5b-2A and 2B)
Figures 2A, 5B:
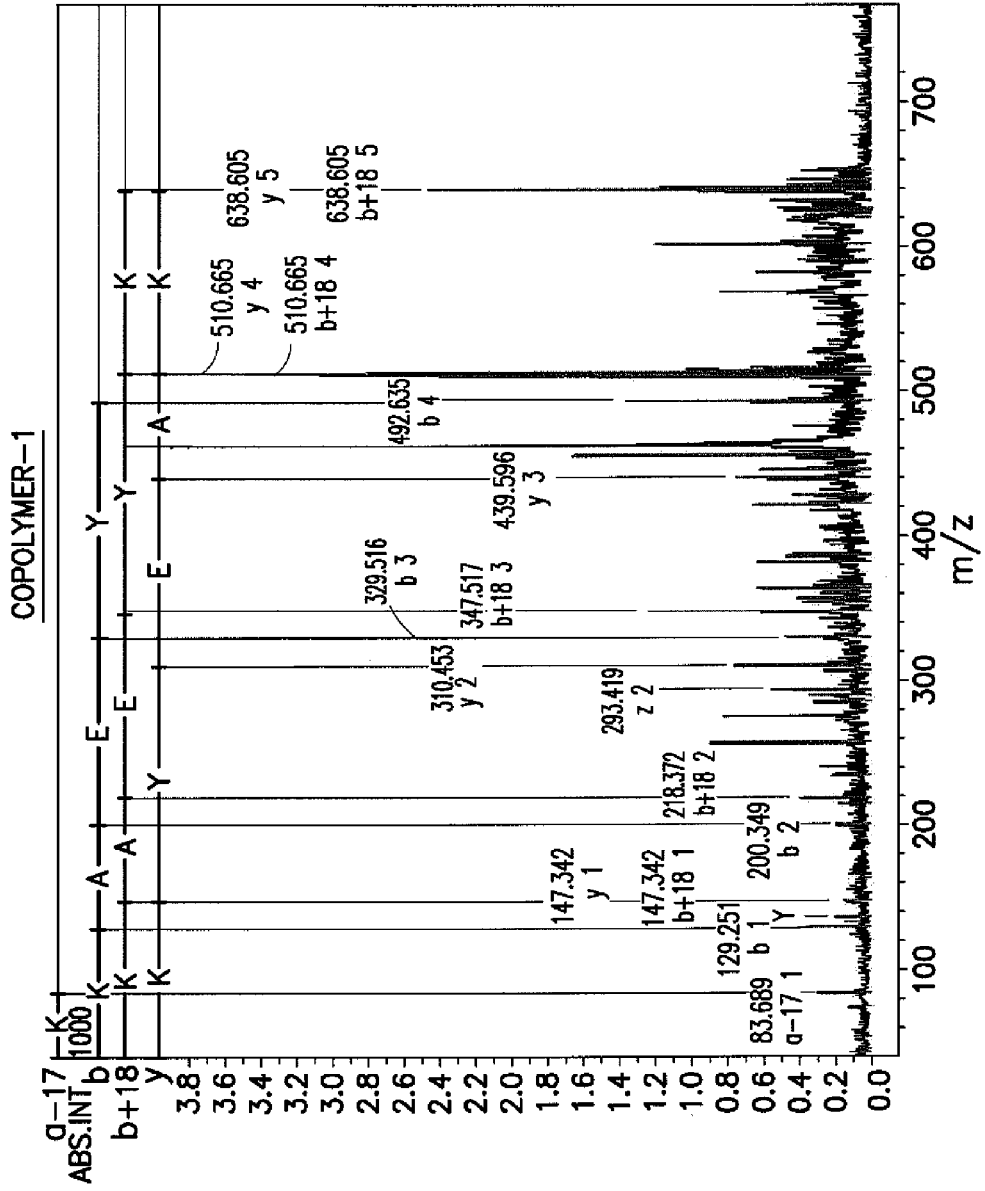
Figures 2, 6A:
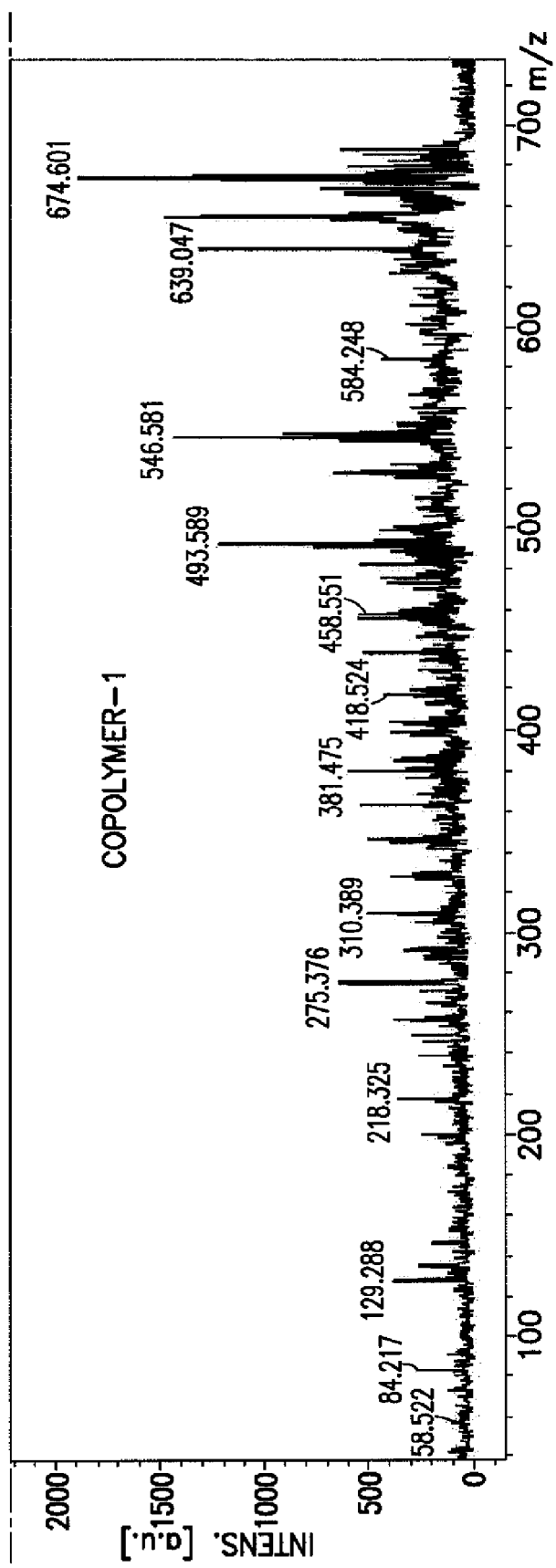
FIG. 6a: MS/MS spectra of m/z 674.880 recorded from enzyme-digested Copaxone (FIG. 6a-1) and Copolymer-1 (FIG. 6a-2)
Figures 1A, 6B:
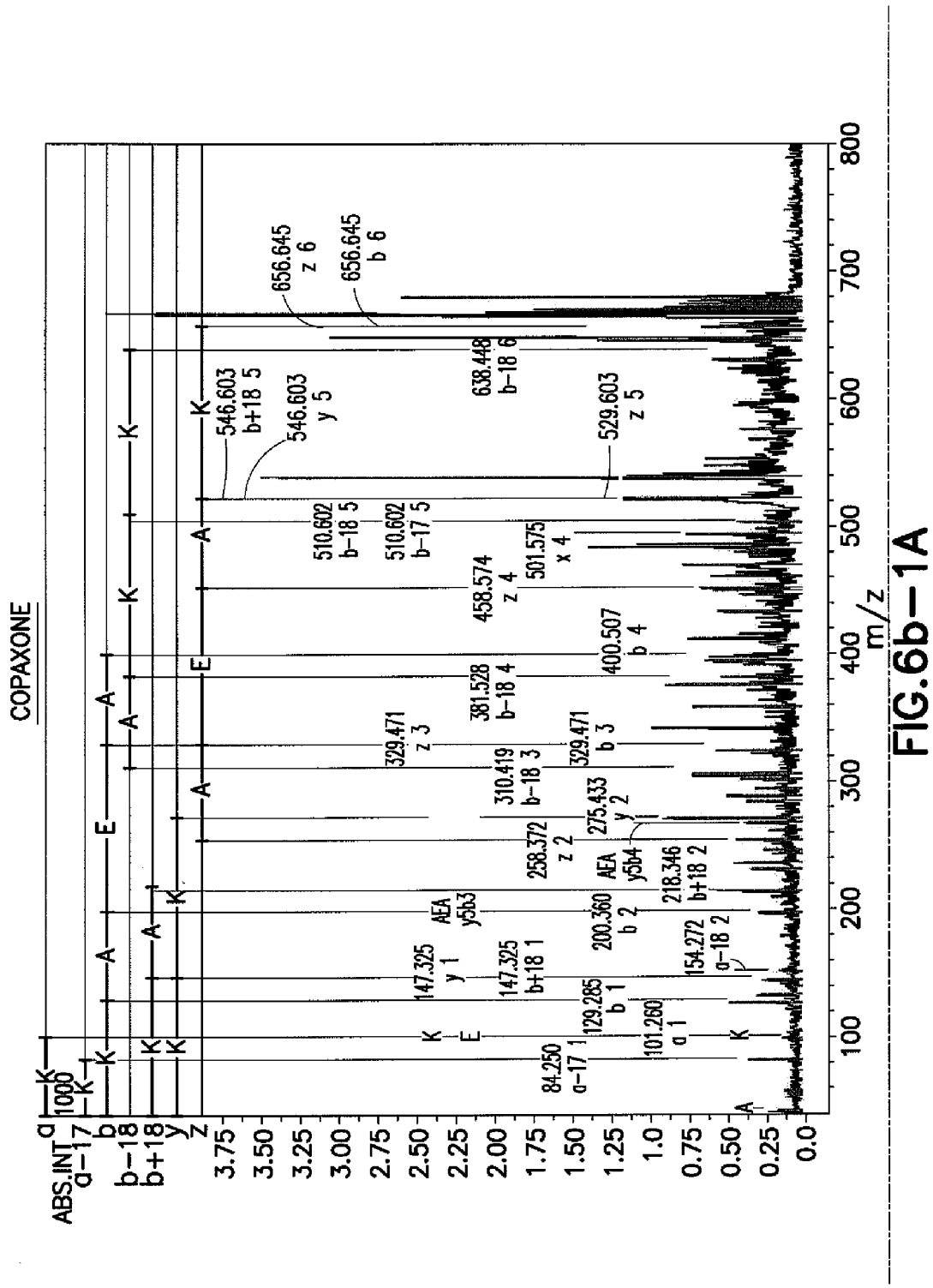
FIG. 6b: Sequence and fragment ions of m/z 674.880 of enzyme-digested Copaxone (FIG. 6b-1A and 1B) and Copolymer-1 (FIG. 6b-2A and 2B)
Figures 2A, 6B:
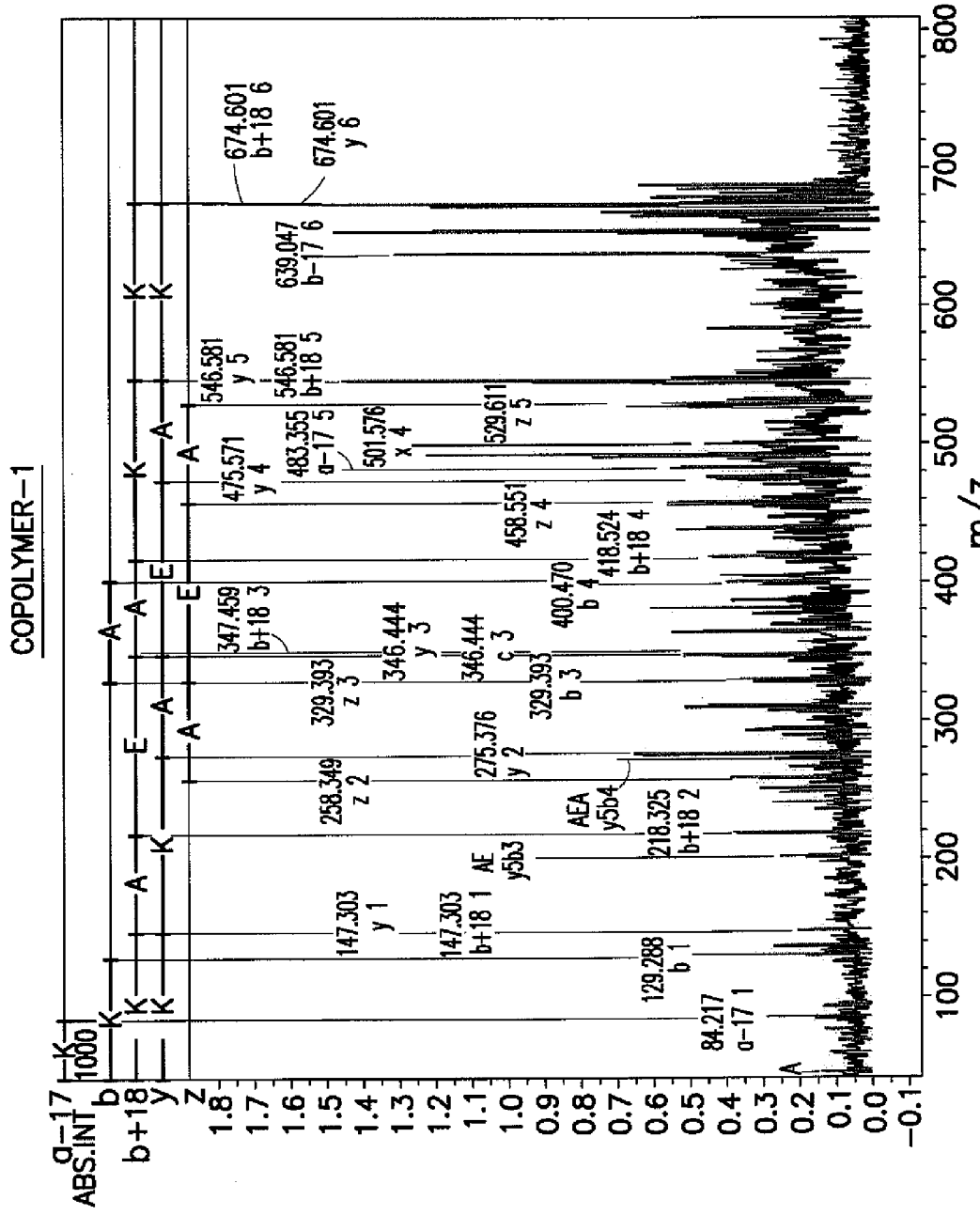
Figures 2, 7A:
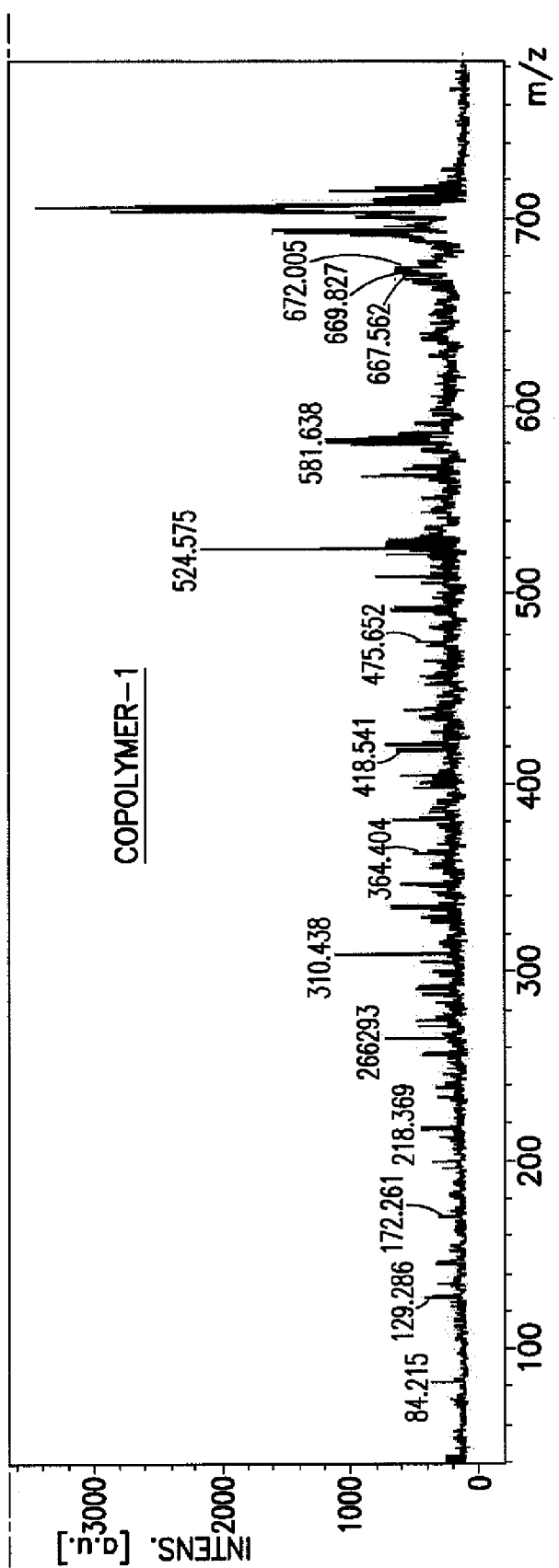
FIG. 7a: MS/MS spectra of m/z 710.622 recorded from enzyme-digested Copaxone (FIG. 7a-1) and Copolymer-1 (FIG. 7a-2)
Figures 1A, 7B:
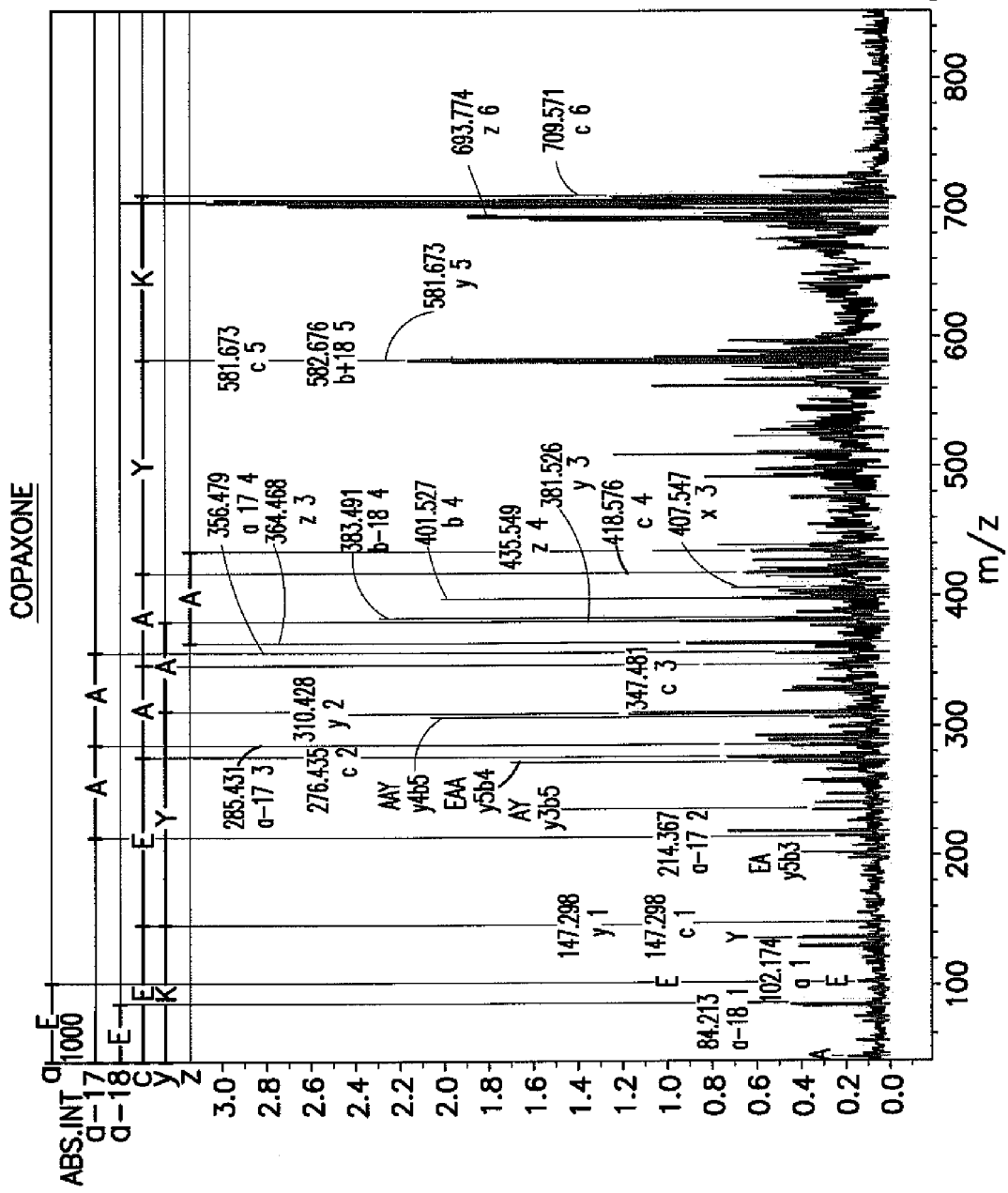
FIG. 7b: Sequence and fragment ions of m/z 710.622 of enzyme-digested Copaxone (FIG. 7b-1A and 1B) and Copolymer-1 (FIG. 7b-2A and 2B)
Figures 2A, 7B:
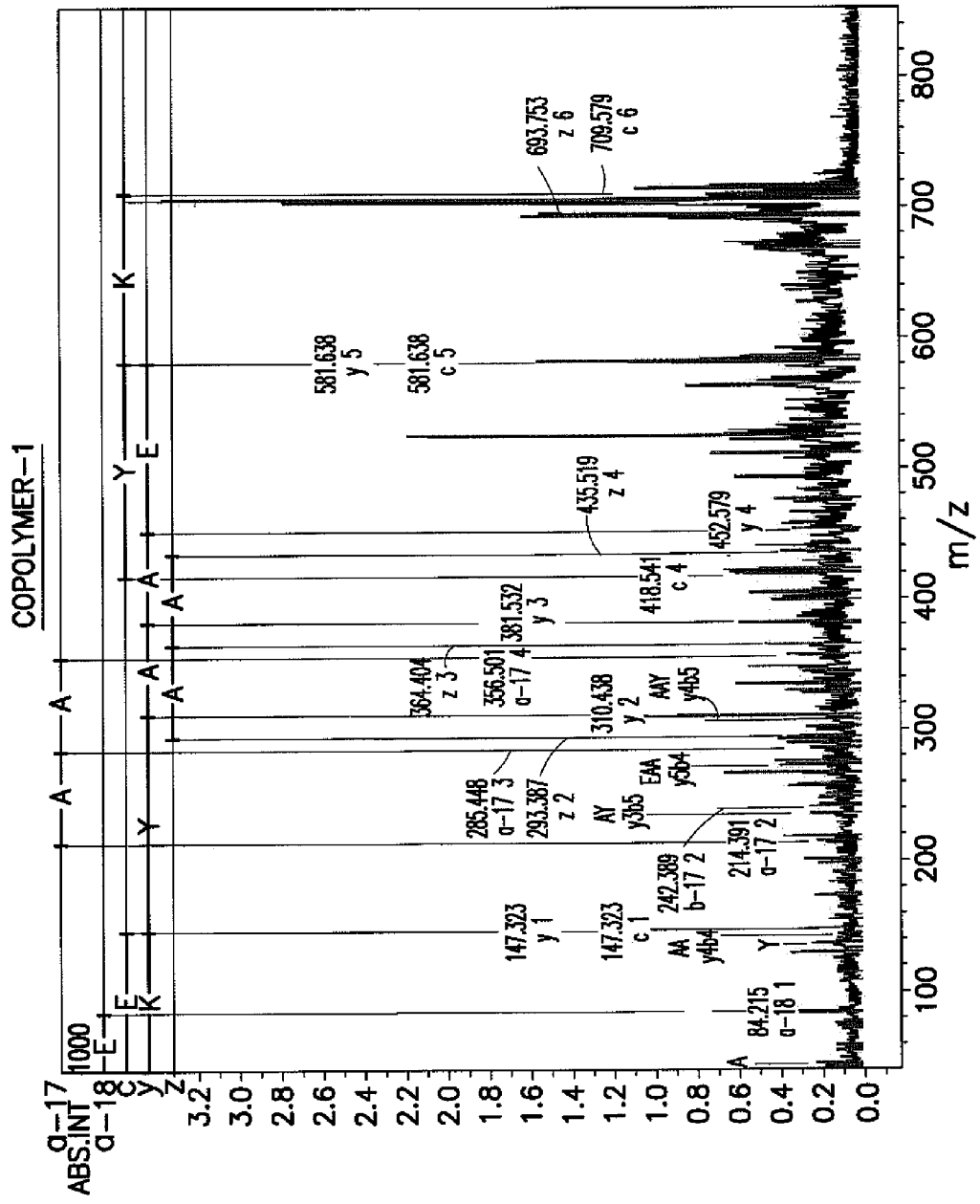
Figures 2, 8A:
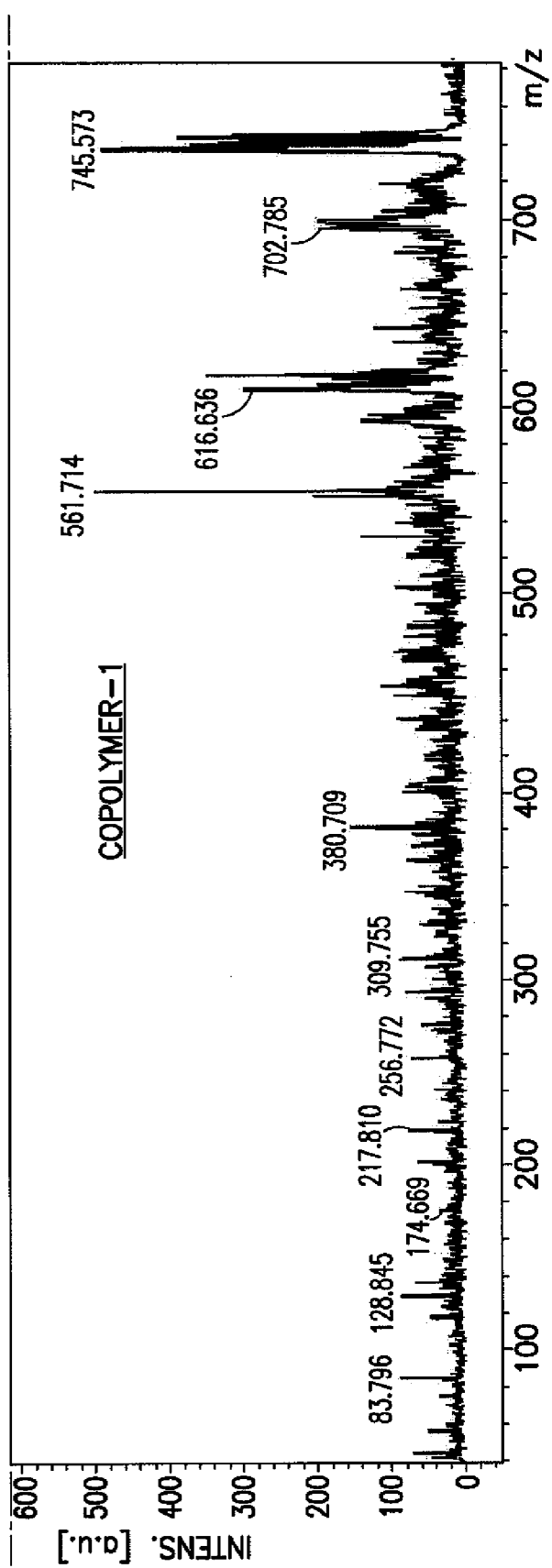
FIG. 8a: MS/MS spectra of m/z 745.568 recorded from enzyme-digested Copaxone (FIG. 8a-1) and Copolymer-1 (FIG. 8a-2)
Figures 2A, 8B:
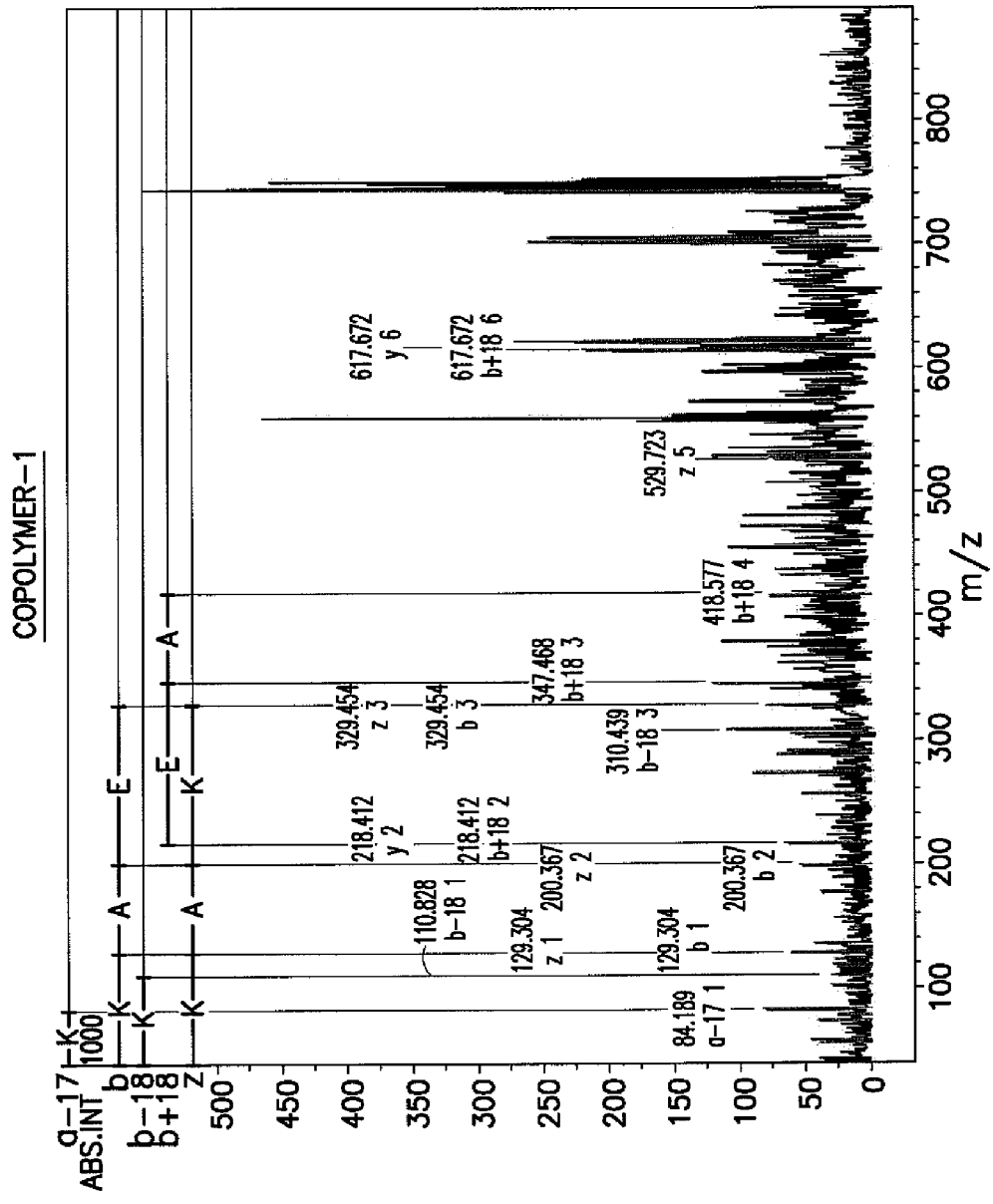
FIG. 8b: Sequence and fragment ions of m/z 745.568 of enzyme-digested Copaxone (FIG. 8b-1A and 1B) and Copolymer-1 (8b-2A and 2B)
Figure 9B:
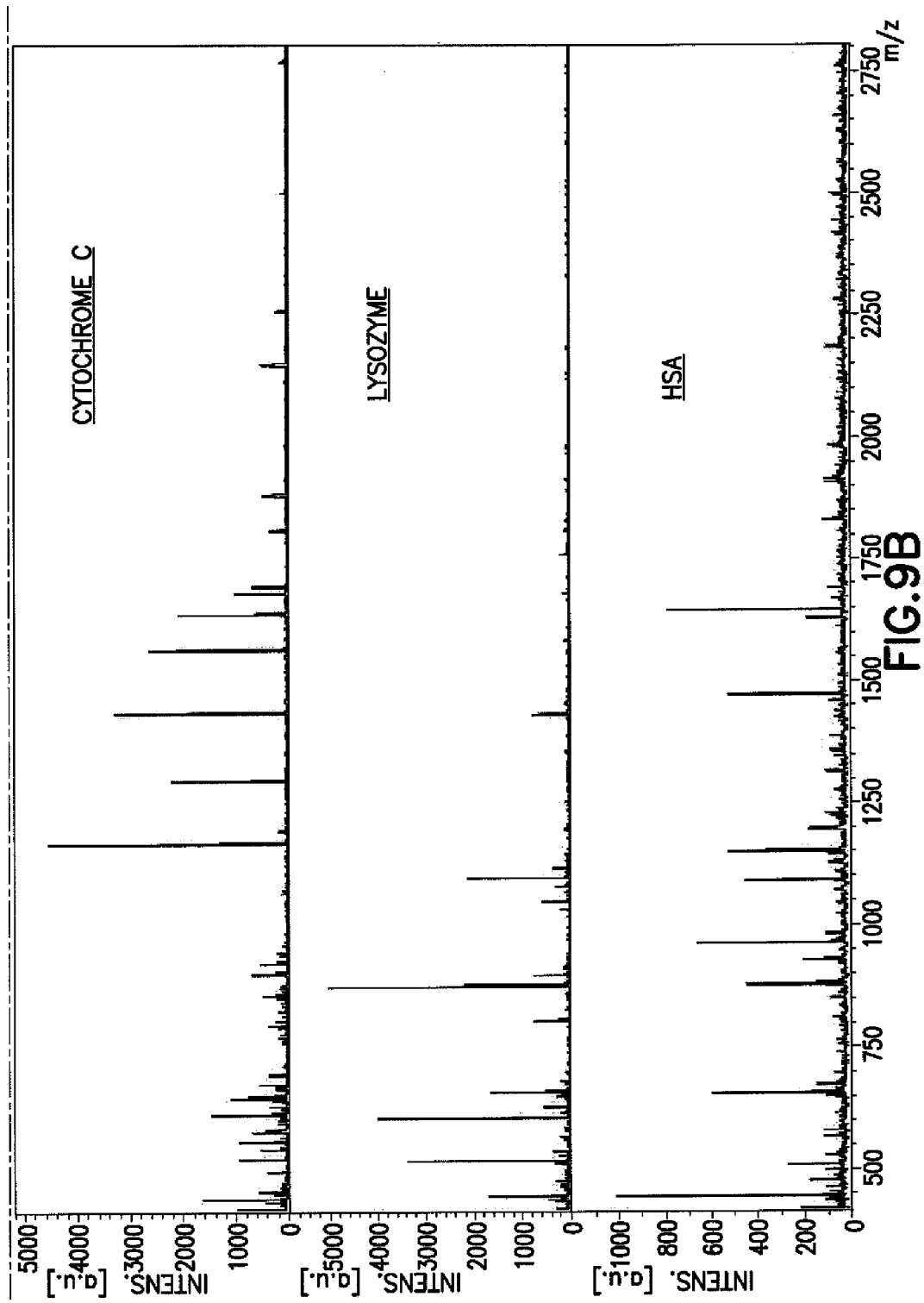
FIGS. 9 A and B: Mass spectra of enzyme-digested Copaxone, Copolymer-1, Cytochrom C, lysozyme and HSA

The present invention provides an approach to evaluate the chemical similarities between two complex molecules. For example, without sample pretreatment, the mass spectra of complex peptides mixtures are the average results of all molecules in the sample and comprise unresolved signals. In order to obtain reproducible and clearly defined spectra to compare the composition of two complex mixtures, the samples are digested to smaller fragments by chemical reactions or enzymatic reactions. Mass spectrometry with tandem MS function is then used to characterize the digested sample.

Multivariate statistic is used to process the obtaining mass spectra into classification. For example, principal component analysis (PCA), a simple and non-parametric method multivariate statistic, is performed for grouping the complex data sets. The mass spectra coupled with multivariate statistic provide comparative information of the complex polypeptide molecules.

To assist in understanding the present invention, the following examples are included which describe the results of a series of experiments. The following examples relating to this invention should not, of course, be construed as specifically limiting the invention. Such variations of the invention, now known or later developed, which would be within the purview of one skilled in the art are considered to fall within the scope of the present invention as hereinafter claimed.

Example 1

Preparation of Protected Copolymer-1

N-carboxyanhydride of L-alanine (4.0 g, 34.78 mmol), N-carboxyanhydride of γ-benzyl L-glutamate (3.0 g, 11.39 mmol), N-carboxyanhydride of N-trifluoroacetyllysine (7.47 g, 27.97 mmol), and N-carboxyanhydride of L-tyrosine (1.6 g, 7.73 mmol) were placed in a single-neck flask with a magnetic stirrer. This mixture was dissolved by adding dry dioxane (289 mL). Distilled diethylamine (60 µL) was added. The resulting mixture was stirred mechanically for 24 hours at room temperature. Acetone (116 mL) was added to the mixture and the solution was slowly poured into a mixture of acetone (173 mL) and water (578 mL). The suspension was stirred and filtered. The solid was dried under vacuum at NMT 45° C. to give 12.02 g protected copolymer-1 (94.7% of yield).

Example 2

Deprotection of Benzyl Group From poly[L-Ala, 5-benzyl-L-Glu, N6-TFA-L-Lys, L-Tyr] to poly[L-Ala, L-Glu, N6-TFA-L-Lys, L-Tyr]

12.02 g of protected copolymer-1, from Example 1, was suspended in 72 mL of 33% HBr/HOAc. The mixture was stirred at room temperature for 17 hours and the solution became clear. The mixture was extracted and washed with n-heptane (190 mL). The lower layer of the mixture was transferred into a mixture of water (240 mL) and n-heptane (120 mL). The precipitate was filtrated and dried to give trifluoroacetyl-glatiramer as a white solid.

Example 3

Deprotection of Trifluoroacetyl Group From poly[L-Ala, L-Glu, N6-TFA-L-Lys, L-Tyr] to poly[L-Ala, L-Glu, L-Lys, L-Tyr]

9.5 g of trifluoroacetyl-glatiramer, from Example 2 was reacted with water (120.2 mL) and 40% tetrabutylammonium hydroxide in water (52.2 mL, 3 eq) for 24 hours at room temperature. The pH of the mixture was adjusted to 3~4 by acetic acid (20 mL) to give a glatiramer acetate solution, and ultrafiltration was conducted by using a 3 kilodalton membrane to remove the low-molecular weight impurities. After 2 cycles of continuous water ultrafiltration, the resulting product is concentrated and lyophilized to give glatiramer acetate (Copolymer-1) as a pure white solid (4.7 g, 60% yield).

Example 4

Peptide Standard Digestion and MS Analysis

Copaxone was diluted to 0.04 mg/100 µl with 80 mM $NH_4HCO_3$ and digested with Trypsin (1 µg/100 µl) for 30 minutes at 57° C. MALDI/TOF/TOF (Autoflex III, Bruker Daltonics Corp.). Analysis was performed with dried and co-crystallized mixture of 1 µl digested Copaxone with 1 µl solution of MALDI matrix α-CHC. Reflective positive mode (RP) and linear positive mode (LP) on the mass spectrometer were used to detect the peptides. Based on the high-resolution analytical results of RP mode, precursor ions are selected for TOF/TOF mass spectrometry analysis. This is a peptide standard that provides the peptide fragments as the fingerprint for comparison with other samples.

Example 5

Application for the Analysis of Other Peptides

Copolymer-1,3-NCAs (N-carboxyanhydrides) and 4-NCAs synthesized from the above examples and three protein standards (Cytochrom C, lysozyme and HSA) were also detected and analyzed according to the above method of example 4. 3-NCAs is composed of Lys, Glu, and Tyr at the equivalent ratio of 3.5:1.45:1.0. As compared to Copaxone and Copolymer-1,3-NCAs lacks amino acid alanine. 4-NCAs is composed of Phe, Lys, Glu, and Tyr at the equivalent ratio of 4.0:3.5:1.45:1.0. In 4-NCAs, the hydrophilic Ala in Copaxone is substituted by the hydrophobic Phe and Phe accounts for the highest proportion of the composition (40%). Thus 4-NCAs is hardly soluble in water.

Example 6

Data Processing and Statistical Analysis

Figure 10:
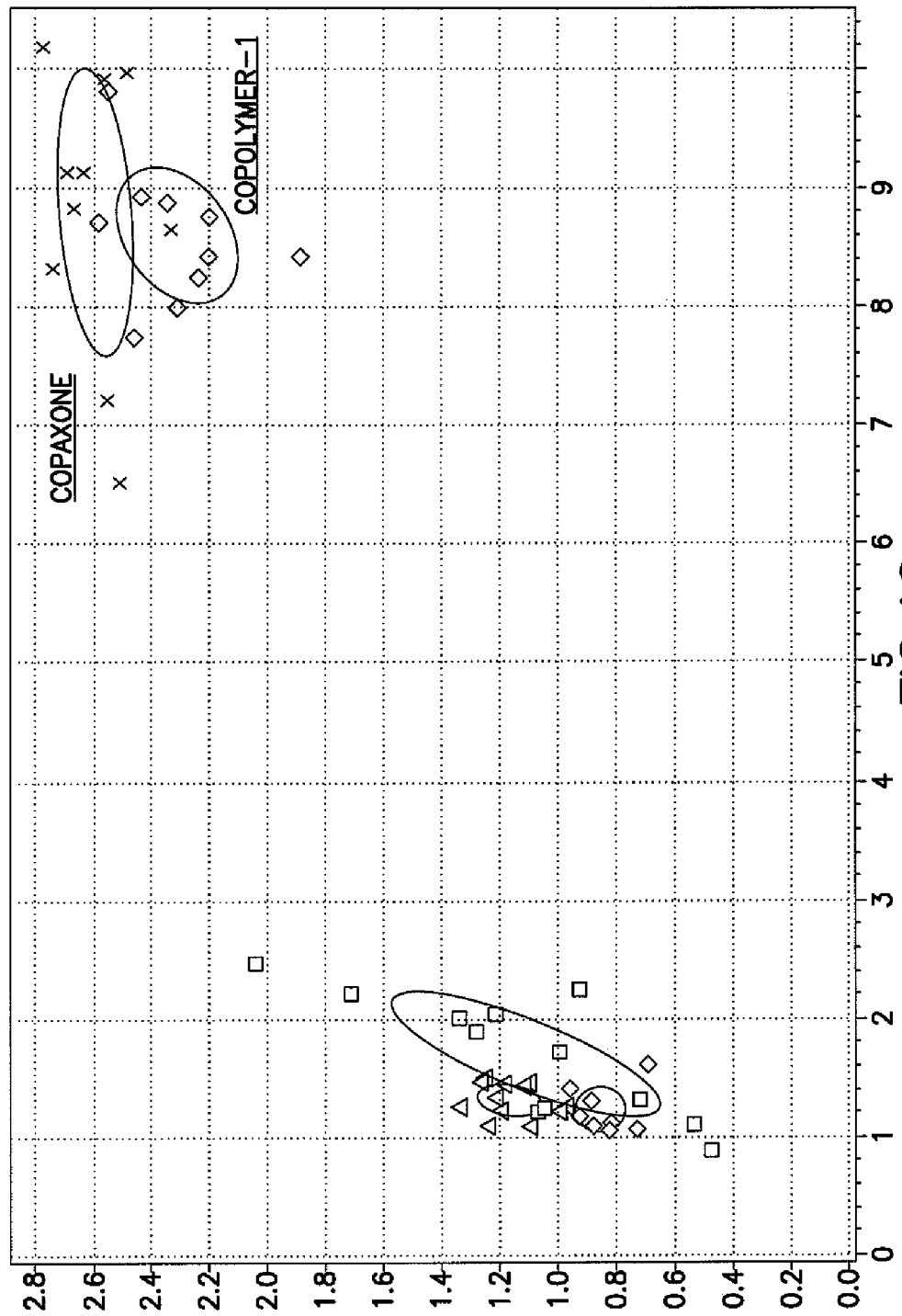
FIG. 10: 2D peaks distribution from the first two peaks based on univariate peak ranking for mass spectra of enzyme-digested Copaxone, Copolymer-1, Cytochrom C, lysozyme and HSA
Figure 11A:
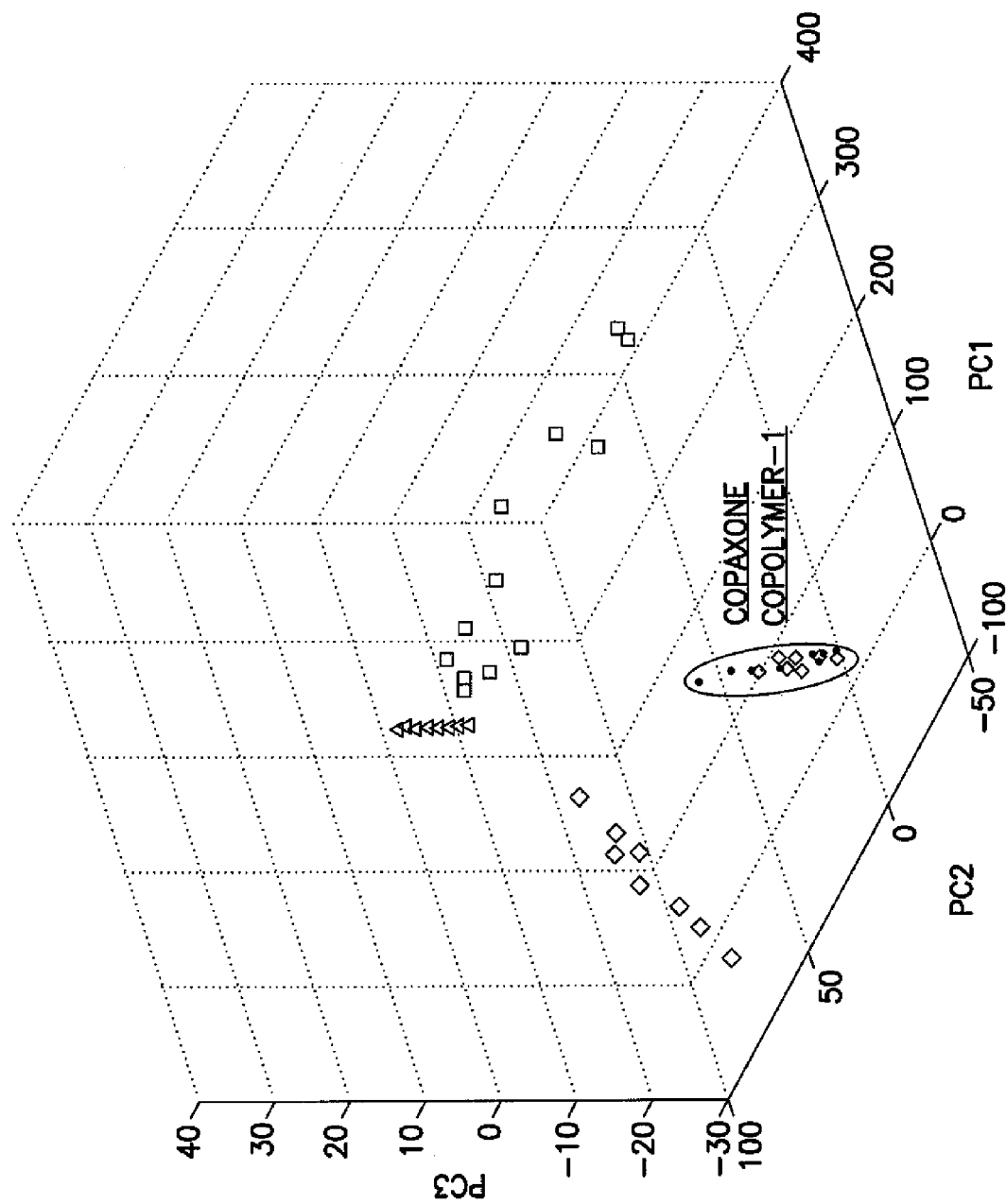
FIG. 11A: 3D patterns of PCA analysis result of Copaxone, Copolymer-1, Cytochrom C, lysozyme and HSA

Firstly, the signals from the first mass and secondary mass spectrometry of the digested Copaxone and the digested sample of copolymer-1 are compared by Flexanalysis and BioTools mass spectrometry software (FIGS. 1-9). Secondly, ClinProTools software was used to process for classification based on univariate peak ranking by statistic test (FIGS. 10 and 12). Finally, Principal Component Analysis (PCA) method was used to process the statistical analysis of the result from mass spectrometry for the reference standard and for the samples (FIGS. 11 and 13). The analytical software is as below:

(a) Flexanalysis

FlexAnalysis is software from Bruker Daltonics Inc. for MALDI-TOF image analysis and processing.

(b) BioTools™

BioTools™ is software from Bruker Daltonics Inc. to support mass spectrometry-based proteomics. It is designed for the interpretation of mass spectra of protein digests or peptides obtained with Bruker Daltonics ESI and MALDI instruments. It can also serve as an interface to database search.

(c) ClinProTools

ClinProTools is statistical analysis software from Bruker Daltonics Inc. to process mainly mass spectra of proteins or peptides from MALDI/TOF instruments. ClinProTools combines multiple mathematical algorithms to generate pattern recognition models for statistics and classification.

The invention claimed is:
1. A method of analyzing a complex molecule, comprising the steps of:
   a) providing a test sample comprising the complex molecule, wherein the test sample has not been pretreated and/or pre-separated;
   b) digesting or decomposing the complex molecule to produce fragments and obtain a digested or decomposed sample comprising the fragments;
   c) analyzing the digested or decomposed sample directly with a mass spectroscopy to provide spectra; and
   d) analyzing the spectra by a Principal Component Analysis (PCA) statistical analysis method directly;
   e) providing a reference standard sample;

f) subjecting the reference standard sample to steps b)-d) as recited above; and
g) comparing the result of the PCA analysis in connection with the test sample with the result of the PCA analysis in connection with the reference standard sample to determine similarity between the test sample and reference standard sample.

2. The method according to claim 1, wherein the complex molecule is selected from the group consisting of a peptide, a peptide mixture, a polypeptide mixture, a protein, a protein mixture, a biologic and a biosimilar.

3. The method according to claim 2, wherein the complex molecule is a biosimilar.

4. The method according to claim 3, wherein the biosimilar is a monoclonal antibody.

* * * * *